US007297846B2

(12) United States Patent
Van Der Valk et al.

(10) Patent No.: US 7,297,846 B2
(45) Date of Patent: Nov. 20, 2007

(54) **GRASSES EXPRESSING *AT*H1 EXHIBIT DELAYED HEADING AND REDUCED INFLORESCENSES**

(75) Inventors: Pieter Van Der Valk, Rilland (NL); Cornelius M. P. Van Dun, Roosendaal (NL); Sjef C. M. Smeekens, Driebergen (NL); Marcel C. G. Proveniers, Utrecht (NL)

(73) Assignee: Advanta Seeds B.V., Kapelle (NL)

( * ) Notice: Subject to any disclaimer, the term of this patent is extended or adjusted under 35 U.S.C. 154(b) by 490 days.

(21) Appl. No.: 10/344,975

(22) PCT Filed: Aug. 16, 2001

(86) PCT No.: PCT/EP01/09570

§ 371 (c)(1),
(2), (4) Date: Jul. 24, 2003

(87) PCT Pub. No.: WO02/14486

PCT Pub. Date: Feb. 21, 2002

(65) Prior Publication Data

US 2005/0183172 A1    Aug. 18, 2005

Related U.S. Application Data

(63) Continuation-in-part of application No. 09/423,575, filed on Jan. 27, 2000, now Pat. No. 6,864,051.

(60) Provisional application No. 60/300,220, filed on Jun. 22, 2001, provisional application No. 60/253,274, filed on Nov. 27, 2000, provisional application No. 60/253,327, filed on Nov. 27, 2000, provisional application No. 60/226,422, filed on Aug. 18, 2000.

(30) Foreign Application Priority Data

May 14, 1997    (GB)    ................... 9709789.3
Dec. 30, 1997    (GB)    ................... 9727458.3

(51) Int. Cl.
*A01H 5/00*    (2006.01)
*C12N 15/82*    (2006.01)

(52) U.S. Cl. ..................... 800/320; 800/290; 800/278; 435/419; 435/468

(58) Field of Classification Search ..................... None
See application file for complete search history.

(56) References Cited

U.S. PATENT DOCUMENTS 5,744,693 A    4/1998    Meyerowitz et al.
6,864,051 B1    3/2005    Smeekens et al.
2005/0120403 A1*    6/2005    Van Der Valk ............. 800/278

FOREIGN PATENT DOCUMENTS

WO    WO 98/51800    * 11/1998
WO    WO 98/51800 A1    11/1998
WO    WO 99/05286 A1    2/1999
WO    WO 00/32780 A1    6/2000
WO    WO 00/37488 A2    6/2000

OTHER PUBLICATIONS

Lesniewska A. et al. (2001) Androgenesis from *Festuca pratensis* X *Lolim multiflorum* amphidiploid cultivars in order to select and stabilize rare gene combinations for grass breeding. Hereditary. vol. 86, pp. 167-176.*
Quaidvilieg N. et al. The homeobox gene ATH1 of Arabidopsis is derepressed in the photomorphogenic mutants cop1 and det1. (1995) The Plant Cell, vol. 7, pp. 117-129.*
Zhang L-H. et al. Differentiation of bermudagrass (Cynodon spp.) genotypes by AFLP analyses. (1999) Theor Appl Genet, vol. 98, pp. 895-902.*
Albright Seed Company. Grass mixes and blends: the best of all traits. (1998) Streamline Publications, World Wide Web. albrightseed.com/grassmixes.htm; pp. 1-2.*
Merriam-Webster's Collegiate Dictionary, 10th Edition. Copyright 1993. Merriam-Webster, Incorporated; Springfield Massachusetts, U.S.A.; p. 510.*
Toki, S., et al., "Expression of a Maize Ubiquitin Gene Promoter-*bar* Chimeric Gene in Transgenic Rice Plants," *Plant Physiol.* 100:1503-1507, 1992.
Aoyama, T., et al., "Ectopic Expression of the Arabidopsis Transcriptional Activator Athb-1 Alters Leaf Cell Fate in Tobacco," *Plant Cell* 7:1773-1785, 1995.
Christensen, A.H., et al., "Maize Polyubiquitin Genes: Structure, Thermal Perturbation of Expression and Transcript Splicing, and Promoter Activity Following Transfer to Protoplasts by Electroporation," *Plant Molecular Biology* 18:675-689, 1992.
Chuck, G., et al., "*KNAT1* Induces Lobed Leaves With Ectopic Meristems When Overexpressed in Arabidopsis," *Plant Cell* 81277-1289, 1996.
Evans, L.T., et al., "Gibberellin Structure and Florigenic Activity in *Lolium temulentum*, a Long-Day Plant," *Planta* 182:97-106, 1990.
Filner, J.J., et al., "Development of the Particle Inflow Gun for DNA Delivery to Plant Cells," *Plant Cell Reports* 11:323-328, 1992.
Leśniewska, A., et al., "Androgenesis From *Festuca pratensis* × *Lolium multiflorum* Amphidiploid Cultivars in Order to Select and Stabilize Rare Gene Combinations for Grass Breeding," *Heredity* 86:167-176, 2001.

(Continued)

*Primary Examiner*—Anne Kubelik
*Assistant Examiner*—Cathy Kingdon Worley
(74) *Attorney, Agent, or Firm*—Christensen O'Connor Johnson Kindness PLLC

(57) ABSTRACT

Novel grass plants, their progeny, and parts thereof are disclosed which have been genetically modified by introduction of a nucleic acid molecule encoding the transcription factor AtH1. This modification causes a heritable change in one or more plant characteristics such as, for example, inhibition of flowering, absence of inflorescence, increased production of tillers, delayed heading, and inhibition of the developmental switch from vegetative to generative growth.

17 Claims, 17 Drawing Sheets

OTHER PUBLICATIONS

Lincoln, C., et al., "A *Knotted1*-Like Homeobox Gene In Arabidopsis Is Expressed in the Vegetative Meristem and Dramatically Alters Leaf Morphology When Overexpressed in Transgenic Plants," *Plant Cell 6*:1859-1876, 1994.

McElroy, D., et al., "Construction of Expression Vectors Based on the Rice Actin 1 (*Act1*) 5' Region for Use in Monocot Transformation," *Molecular and General Genetics 231*:150-160, 1991.

Neilsen, K.A., and E. Knudsen, "Regeneration of Green Plants From Embryogenic Suspension Cultures of Kentucky Blue Grass (*Poa pratensis* L.)," *Journal of Plant Physiology 141*:589-595, 1993.

Proveniers, M., and S. Smeekens, "The Arabidopsis Homeobox Gene *ATH1* and Floral Transition," 1997.

Robson, P.R.H., et al., "Genetic Engineering of Harvest Index in Tobacco Through Overexpression of a Phytochrome Gene," *Nature Biotechnology 14*(8):995-998, 1996.

Stadelmann, F.J., et al., "Field Performance of Cell-Suspension-Derived *Lollium perenne* L. Regenerants and Their Progenies," *Theoretical and Applied Genetics 96*:634-639, 1998.

Spangenberg, G., et al., "Transgenic Perennial Ryegrass (*Lolium perenne*) Plants From Microprojectile Bombardment of Embryogenic Suspension Cells," *Plant Science 108*:209-217, 1995.

Spangenberg, G., et al., "Transgenic Tall Fescue (*Festuca arundinacea*) and Red Fescue (*F. rubra*) Plants from Microprojectile Bombardment of Embryogenic Suspension Cells," *Journal of Plant Physiology 145*:693-701, 1995.

\* cited by examiner

FIG. 6, cont

```
   1 aattcgggcc caattcgccc tatagtgagt cgtattacaa
  41 ttcactggcc gtcgttttac aacgtcgtga ctgggaaaac
  81 cctggcgtta cccaacttaa tcgccttgca gcacatcccc
 121 ctttcgccag ctggcgtaat agcgaagagg cccgcaccga
 161 tcgcccttcc aacagttgcg cagcctgaa tggcgaatgg
 201 acgcgccctg tagcggcgca ttaagcgcgg cgggtgtggt
 241 ggttacgcgc agcgtgaccg ctacacttgc cagcgcccta
 281 gcgcccgctc ctttcgcttt cttcccttcc tttctcgcca
 321 cgttcgccgg ctttccccgt caagctctaa atcgggggct
 361 ccctttaggg ttccgattta gtgctttacg gcacctcgac
 401 cccaaaaaac ttgattaggg tgatggttca cgtagtgggc
 441 catcgccctg atagacggtt tttcgccctt tgacgttgga
 481 gtccacgttc tttaatagtg gactcttgtt ccaaactgga
 521 acaacactca accctatctc ggtctattct tttgatttat
 561 aagggatttt gccgatttcg gcctattggt taaaaatga
 601 gctgatttaa caaaaattta acgcgaattt taacaaaata
 641 ttaacgctta caatttcctg atgcggtatt ttctccttac
 681 gcatctgtgc ggtatttcac accgcatcag gtggcacttt
 721 tcggggaaat gtgcgcggaa cccctatttg tttatttttc
 761 taaatacatt caaatatgta tccgctcatg agacaataac
 801 cctgataaat gcttcaataa tattgaaaaa ggaagagtat
 841 gagtattcaa catttccgtg tcgcccttat tccctttttt
 881 gcggcatttt gccttcctgt ttttgctcac ccagaaacgc
 921 tggtgaaagt aaaagatgct gaagatcagt tgggtgcacg
 961 agtgggttac atcgaactgg atctcaacag cggtaagatc
1001 cttgagagtt ttcgccccga agaacgtttt ccaatgatga
1041 gcacttttaa agttctgcta tgtggcgcgg tattatcccg
1081 tattgacgcc gggcaagagc aactcggtcg ccgcatacac
1121 tattctcaga atgacttggt tgagtactca ccagtcacag
1161 aaaagcatct tacggatggc atgacagtaa gagaattatg
1201 cagtgctgcc ataaccatga gtgataacac tgcggccaac
1241 ttacttctga caacgatcgg aggaccgaag gagctaaccg
1281 cttttttgca caacatgggg gatcatgtaa ctcgccttga
1321 tcgttgggaa ccggagctga atgaagccat accaaacgac
1361 gagcgtgaca ccacgatgcc tgtagcaatg gcaacaacgt
1401 tgcgcaaact attaactggc gaactactta ctctagcttc
1441 ccggcaacaa ttaatagact ggatggaggc ggataaagtt
1481 gcaggaccac ttctgcgctc ggcccttccg gctggctgt
1521 ttattgctga taaatctgga gccggtgagc gtgggtctcg
1561 cggtatcatt gcagcactgg ggccagatgg taagccctcc
1601 cgtatcgtag ttatctacac gacggggagt caggcaacta
1641 tggatgaacg aaatagacag atcgctgaga taggtgcctc
1681 actgattaag cattggtaac tgtcagacca gtttactca
1721 tatatacttt agattgattt aaaacttcat ttttaattta
1761 aaaggatcta ggtgaagatc cttttttgata atctcatgac
1801 caaaatccct taacgtgagt tttcgttcca ctgagcgtca
1841 gaccccgtag aaaagatcaa aggatcttct tgagatcctt
1881 tttttctgcg cgtaatctgc tgcttgcaaa caaaaaaacc
1921 accgctacca gcggtggttt gtttgccgga tcaagagcta
1961 ccaactcttt ttccgaaggt aactggcttc agcagagcgc
2001 agataccaaa tactgttctt ctagtgtagc cgtagttagg
2041 ccaccacttc aagaactctg tagcaccgcc tacataccctc
2081 gctctgctaa tcctgttacc agtggctgct gccagtggcg
2121 ataagtcgtg tcttaccggg ttggactcaa gacgatagtt
2161 accggataag gcgcagcggt cgggctgaac gggggggttcg
2201 tgcacacagc ccagcttgga gcgaacgacc tacaccgaac
2241 tgagatacct acagcgtgag ctatgagaaa gcgccacgct
2281 tcccgaaggg agaaaggcgg acaggtatcc ggtaagcggc
2321 agggtcggaa caggagagcg cacgagggag cttccagggg
2361 gaaacgcctg gtatctttat agtcctgtcg ggtttcgcca
2401 cctctgactt gagcgtcgat ttttgtgatg ctcgtcaggg
2441 gggcggagcc tatggaaaaa cgccagcaac gcggcctttt
2481 tacggttcct ggccttttgc tggccttttg ctcacatgtt
2521 ctttcctgcg ttatcccctg attctgtgga taaccgtatt
2561 accgcctttg agtgagctga taccgctcgc cgcagccgaa
2601 cgaccgagcg cagcgagtca gtgagcgagg aagcggaaga
2641 gcgcccaata cgcaaaccgc ctctccccgc gcgttggccg
2681 attcattaat gcagctggca cgacaggttt cccgactgga
2721 aagcgggcag tgagcgcaac gcaattaatg tgagttagct
2761 cactcattag gcacccagg ctttacactt tatgcttccg
2801 gctcgtatgt tgtgtggaat tgtgagcgga taacaatttc
2841 acacaggaaa cagctatgac catgattacg ccaagctatt
```

```
2881  taggtgacac tatagaatac tcaagctatg catccaacgc
2921  gttgggagct ctcccatatg gtcgacctgc aggcggccgc
2961  ctagagataa tgagcattgc atgtctaagt tataaaaaat
3001  taccacatat tttttttgtc acacttgttt gaagtgcagt
3041  ttatctatct ttatacatat atttaaactt tactctacga
3081  ataatataat ctatagtact acaataatat cagtgtttta
3121  gagaatcata taaatgaaca gttagacatg gtctaaagga
3161  caattgagta ttttgacaac aggactctac agttttatct
3201  ttttagtgtg catgtgttct ccttttttt tgcaaatagc
3241  ttcacctata taatacttca tccattttat tagtacatcc
3281  atttagggtt tagggttaat ggttttata gactaatttt
3321  tttagtacat ctattttatt ctattttagc ctctaaatta
3361  agaaaactaa aactctattt tagtttttt atttaataat
3401  ttagatataa aatagaataa aataaagtga ctaaaaatta
3441  aacaaatacc ctttaagaaa ttaaaaaaac taaggaaaca
3481  tttttcttgt ttcgagtaga taatgccagc ctgttaaacg
3521  ccgtcgacga gtctaacgga caccaaccag cgaaccagca
3561  gcgtcgcgtc gggccaagcg aagcagacgg cacggcatct
3601  ctgtcgctgc ctctggaccc ctctcgagag ttccgctcca
3641  ccgttggact tgctccgctg tcggcatcca gaaattgcgt
3681  ggcggagcgg cagacgtgag ccggcacggc aggcggcctc
3721  ctcctcctct cacggcaccg gcagctacgg gggattcctt
3761  tcccacccgct ccttcgcttt ccttcctcg cccgccgtaa
3801  taaatagaca cccctccac accctcttc cccaacctcg
3841  tgttgttcgg agcgcacaca cacacaacca gatctcccc
3881  aaatccaccc gtcggcacct ccgcttcaag gtacgccgct
3921  cgtcctcccc cccccccct ctctaccttc tctagatcgg
3961  cgttccggtc catggttagg gcccggtagt tctacttctg
4001  ttcatgtttg tgttagatcc gtgtttgtgt tagatccgtg
4041  ctgctagcgt tcgtacacgg atgcgacctg tacgtcagac
4081  acgttctgat tgctaacttg ccagtgtttc tctttgggga
4121  atcctgggat ggctctagcc gttccgcaga cgggatcgat
4161  ttcatgattt tttttgtttc gttgcatagg gtttggtttg
4201  cccttttcct ttatttcaat atatgccgtg cacttgtttg
4241  tcgggtcatc ttttcatgct ttttttgtc ttggttgtga
4281  tgatgtggtc tggttgggcg gtcgttctag atcggagtag
4321  aattctgttt caaactacct ggtggattta ttaattttgg
4361  atctgtatgt gtgtgccata catattcata gttacgaatt
4401  gaagatgatg gatgaaata tcgatctagg ataggtatac
4441  atgttgatgc gggttttact gatgcatata cagagatgct
4481  ttttgttcgc ttggttgtga tgatgtggtg tggttgggcg
4521  gtcgttcatt cgttctagat cggagtagaa tactgtttca
4561  aactacctgg tgtatttatt aattttggaa ctgtatgtgt
4601  gtgtcataca tcttcatagt tacgagttta agatggatgg
4641  aaatatcgat ctaggatagg tatacatgtt gatgtgggtt
4681  ttactgatgc atatacatga tggcatatgc agcatctatt
4721  catatgctct aaccttgagt acctatctat tataataaac
4761  aagtatgttt tataattatt ttgatcttga tatacttgga
4801  tgatggcata tgcagcagct atatgtggat tttttagcc
4841  ctgccttcat acgctattta tttgcttggt actgtttctt
4881  ttgtcgatgc tcaccctgtt gtttggtgtt acttctgcag
4921  gtcgacccaa tggacaacaa caacaacaac aacacttta
4961  gttctctgga taatgtcatg actaaccaaa atcctcttct
5001  catggatttt ataccttcaa gagaagattc aacttcattc
5041  tcaacaatgc ttccatggaa taccatcaga tcagatcctc
5081  tacaaatggg tggctttgat attttcaatt ctatgctgac
5121  taacaaatac ttatcatctt ctccacggtc tatcgatgtt
5161  caagataacc gcaatgttga gttcatggct cctcctcctc
5201  atcctcctcc acttcatcct ttggatcatt taagacacta
5241  tgatgattcc tcaaacaaca tgtggggttt tgaagcaaat
5281  agtgagtttc aggcattttc aggtgtagtt ggtccaagtg
5321  aaccaatgat gtctacattc ggtgaagaag atttcccgtt
5361  tctaatttcg aataaaagaa acaatgagct ttcattgagt
5401  cttgcatcag atgtttctga tgaatgctcg gagataagtc
5441  tttgtgcagc tacaagatta gcctcagagc aagcttcttg
5481  cagcagcaaa gacatttcta ataacgttgt tactcaaggt
5521  ttctctcaac ttatatttgg ctcaaaatac cttcactctg
5561  ttcaagaaat actatctcat ttcgccgcat actcgctcga
5601  ttattcatct cgaggaaccg agtcaggagc tgctagttca
5641  gcctttactt cacgttttga gaatataact gagtttcttg
5681  atggtgattc taataactcg gaggcgggtt tcggatctac
5721  atttcaaagg agagcattag aagcaaagaa aacccatctc
5761  ttggatcttc ttcaaatggt ggatgatcga tatagtcatt
5801  gcgtagatga gattcatacg gttatatcag cgttccatgc
```

FIG. 6, cont.

```
5841  tgcaaccgag ttagatccac agttacacac ccggtttgcc
5881  ctccaaaccg tttccttctt atacaagaac ctgagagaga
5921  gaatctgcaa gaagataatc tctatgggat ctgtattgga
5961  gagaggcaaa gacaagactc aagaaacctc tatgttccac
6001  cagcattgcc ttcttcagca gctgaaacga aagaaccatc
6041  agatttggag acctcaacga ggtttgcctg agaaatctgt
6081  ttcggttcta cggaattgga tgttccaaaa cttccttcac
6121  ccttacccga aagattcgga gaaacatctt ctagctatac
6161  gaagtggctt gacaagaagt caggtatcaa actggtttat
6201  aaatgcgcgg gttaggctat ggaagccgat gatagaagag
6241  atgtatgcgg aaatgaacaa gaggaagctc aataacagtc
6281  acattcaacc caacggacca actcttcgaa tgccaaaatc
6321  tgttatgatg agccaagcaa tgcataaata agacaacaat
6361  tgtgtttacc aactttgtga taattaggca attgctactc
6401  ggatccccga tcgttcaaac atttggcaat aaagtttctt
6441  aagattgaat cctgttgccg gtcttgcgat gattatcata
6481  taatttctgt tgaattacgt taagcatgta ataattaaca
6521  tgtaatgcat gacgttattt atgagatggg tttttatgat
6561  tagagtcccg caattataca tttaatacgc gatagaaaac
6601  aaaatatagc gcgcaaacta ggataaatta tcgcgcgcgg
6641  tgtcatctat gttactagat cgatcgggaa ttgcggccgc
6681  actagcatac tcgaggtcat tcatatgctt gagaagagag
6721  tcgggatagt ccaaaataaa acaaaggtaa gattacctgg
6761  tcaaaagtga aaacatcagt taaaggtgg tataaagtaa
6801  aatatcggta ataaaaggtg gcccaaagtg aaatttactc
6841  ttttctacta ttataaaaat tgaggatgtt tttgtcggta
6881  ctttgatacg tcattttga tgaattggtt tttaagttta
6921  ttcgcttttg gaaatgcata tctgtatttg aatcgggttt
6961  taagttcgtt tgcctttgta aatacagagg gatttgtata
7001  agaaatatct ttaaaaaac ccatatgcta atttgacata
7041  attttgaga aaaatatata ttcaggcgaa ttctcacaat
7081  gaacaataat aagattaaaa tagcttccc ccgttgcagc
7121  gcatgggtat ttttctagt aaaaataaaa gataaactta
7161  gactcaaaac atttacaaaa acaacccta aagttcctaa
7201  agcccaaagt gctatccacg atccatagca abcccagccc
7241  aacccaaccc aacccaaccc accccagtcc agccaactgg
7281  acaatagtct ccabdccccc ccactatcac cgtgagttgt
7321  ccgcacgcac cgcacgtctc gcagccaaaa aaaaaaaaa
7361  gaaagaaaaa aaagaaaaag aaaaaacagc aggtgggtcc
7401  gggtcgtggg ggccggaaac gcgaggagga tcgcgagcca
7441  gcgacgaggc cggccctccc tccgcttcca aagaaacgcc
7481  ccccatcgcc actatataca tacccccccc tctcctccca
7521  tcccccaac cctaccacca ccaccaccac cacctccacc
7561  tcctccccc tcgctgccgg acgacgagct cctccccct
7601  cccctccgc cgccgccgcg ccggtaacca ccccgcccct
7641  ctcctcttc tttctccgtt ttttttccg tctcggtctc
7681  gatctttggc cttggtagtt tgggtgggcg agaggcggct
7721  tcgtgcgcgc ccagatcggt gcgcgggagg ggcgggatct
7761  cgcggctggg gctctcgccg gcgtggatcc ggcccggatc
7801  tcgcggggaa tggggctctc ggatgtagat ctgcgatccg
7841  ccgttgttgg gggagatgat gggggggttta aaatttccgc
7881  catgctaaac aagatcagga agaggggaaa agggcactat
7921  ggtttatatt tttatatatt tctgctgctt cgtcaggctt
7961  agatgtgcta gatctttctt tcttcttttt gtgggtagaa
8001  tttgaatccc tcagcattgt tcatcggtag tttttctttt
8041  catgatttgt gacaaatgca gcctcgtcg gagctttttt
8081  gtaggtagac cggggggcaa tgagatatga aaaagcctga
8121  actcaccgcg acgtctgtcg agaagtttct gatcgaaaag
8161  ttcgacagcg tctccgacct gatgcagctc tcggagggcg
8201  aagaatctcg tgctttcagc ttcgatgtag gagggcgtgg
8241  atatgtctgc gggtaaatag tgcgccgatg gtttctacaa
8281  agatcgttat gtttatcggc actttgcatc ggccgcgctc
8321  ccgattccgg aagtgcttga cattgggaa ttcagcgaga
8361  gcctgaccta ttgcatctcc cgccgtgcac agggtgtcac
8401  gttgcaagac ctgcctgaaa ccgaactgcc cgctgttctg
8441  cagccggtcg cggaggccat ggatgcgatc gctgcggccg
8481  atcttagcca gacgagcggg ttcggcccat tcggaccgca
8521  aggaatcggt caatacacta catgcgtga tttcatatgc
8561  gcgattgctg atccccatgt gtatcactgg caaactgtga
8601  tggacgacac cgtcagtgcg tccgtcgcgc aggctctcga
8641  tgagctgatg ctttgggccg aggactgccc cgaagtccgg
8681  cacctcgtgc acgcggattt cggctccaac aattgcctga
8721  cggacaatgg ccgcataaca gcggtcattg actggagcga
8761  ggcgatgttc ggggattccc aatacgaggt cgccaacatc
```

FIG. 6, cont.

```
8801  ttcttctgga ggccgtggtt ggcttgtatg gagcagcaga
8841  cgcgctactt cgagcggagg catccggagc ttgcaggatc
8881  gccgcggctc cgggcgtata tgctccgcat tggtcttgac
8921  caactctatc agagcttggt tgacggcaat ttcgatgatg
8961  cagcttgggc gcagggtcga tgcgacgcaa tcgtccgatc
9001  cggagccggg actgtcgggc gtacacaaat cgcccgcaga
9041  agcgcggccg gccgtctgga ccgatggctg tgtagaagta
9081  ctcgccgata gtggaaaccg acgcccagc actcgtccgg
9121  gatcctctag agtcgacctg caggcatgcc cgctgaaatc
9161  accagtctct ctctacaaat ctatctctct ctataataat
9201  gtgtgagtag ttcccagata agggaattag ggttcttata
9241  gggtttcgct catgtgttga gcatataaga aacccttagt
9281  atgtatttgt atttgtaaaa tacttctatc aataaaattt
9321  ctaattccta aaaccaaaat ccaggggtac ccgagctcg
```

FIG. 6, cont.

| Molecular features of pVDH636 | | | |
|---|---|---|---|
| Feature | Start position | End position | Description |
| AmpR | 839 | 1699 | Beta-lactamase gene |
| Ubi(maize)ex/in | 2941 | 4920 | Ubi-promoter from maize |
| ATH1 | 4921 | 6400 | AtH1 gene from Arabidpsis thaliana |
| tNos | 6401 | 6672 | Polyadenylation signal from the nopaline synthase gene from Agrobacterium tumefaciens |
| pACT | 6673 | 7533 | Actin-promoter from rice |
| ex-in-ex | 7534 | 8084 | First exon-intron combination from Ubi-maize |
| hph | 8085 | 9119 | Hygromycin resistance gene from Escherichia coli |
| t35S | 9120 | 9359 | Polyadenylation signal from the 35S gene from Cauliflower mosaic virus |

| Amino acid sequence of AtH1 | | | |
|---|---|---|---|
| 1 | mdnnnnnntf | ssldnvmtnq | npllmdfips redststfstm |
| 41 | lpwntirsdp | lqmggfdifn | smltnkylss sprsidvqdn |
| 81 | rnvefmappp | hppplhpldh | lrhyddssnn mwgfeansef |
| 121 | qafsgvvgps | epmmstfgee | dfpflisnkr nnelslslas |
| 161 | dvsdecseis | lcaatrlase | qascsskdis nnvvtqgfsq |
| 201 | lifgskylhs | vqeilshfaa | ysldyssrgt esgaassaft |
| 241 | srfenitefl | dgdsnnseag | fgstfqrral eakkthlldl |
| 281 | lqmvddrysh | cvdeihtvis | afhaateldp qlhtrfalqt |
| 321 | vsflyknlre | rickkiismg | svlergkdkt qetsmfhqhc |
| 361 | llqqlkrknh | qiwrpqrglp | eksvsvlrnw mfqnflhpyp |
| 401 | kdsekhllai | rsgltrsqvs | nwfinarvrl wkpmieemya |
| 441 | emnkrklnns | hiqpngptlr | mpksvmmsqa mhk |

# GRASSES EXPRESSING AtH1 EXHIBIT DELAYED HEADING AND REDUCED INFLORESCENSES

FIELD OF THE INVENTION

The invention relates to grass plants, their progeny, and parts thereof, which have been genetically modified. This modification causes a heritable change in one or more plant characteristics such as, for example, inhibition of flowering, absence of inflorescence, increased production of tillers, delayed heading, and inhibition of the developmental switch from vegetative to generative growth.

BACKGROUND OF THE INVENTION

The prior art includes grasses that have been mutated such that flowering and production of inflorescences do not occur. These grasses, however, exhibit other unwanted characteristics such as dwarfism, leaf discoloration, root failure, and the like. The phrase "genetically modified" as used herein does not include chemical or irradiation mutagenesis, nor standard hybridization techniques that produce sterile progeny. For example, transformation with a nucleic acid to produce an alteration in the plant's genetic material is within the scope of the invention.

The prior art also includes grasses that have been treated with chemicals or phytohormones to inhibit flowering and production of inflorescences. But genetic modification in accordance with the present invention results in a change in heritable traits and does not require such treatment. Change in one or more characteristics of a genetically modified grass may be at least partially reversed by treatment with a phytohormone.

Additionally, dramatic delay of flowering has been shown in other monocots. In wheat, flowering was inhibited using a gibberellin-degrading enzyme. This wheat, however, evidenced certain deleterious side effects such as dwarfism when in the non-flowering phase. The present invention avoids these deleterious side effects.

Although inhibition of flowering in grasses is considered to be a trait of high agronomic value, we are unaware of any demonstration in the prior art that genetic modification of grass can result in a non-flowering phenotype. The present invention has a number of significant advantages both for grasses bred for forage as well as grasses bred for amenity purposes. These advantages can be summarised as follows:

As a consequence of an extended vegetative growth phase, biomass will be generated continuously in the form of leaf material, which means a significant increase of the yield of well-digestible organic matter.

The loss of nutritional quality of the crop as a consequence of the formation of strongly lignified inflorescences as well as seeds is prevented. The percentage of digestible organic matter of a non-flowering grass is estimated to be about 80% during the whole season whereas this percentage is estimated to be about 60% for a non-genetically modified flowering grass. This reduction in nutritional value is prevented by the present invention and the resulting increase in yield allows a farmer to significantly lower the use of feed additives and thereby minimise the overall emission of minerals into the environment.

Amenity grasses are improved in appearance and functional properties due to increased tillering and the absence or reduction of inflorescences.

Pollen development is blocked by a male-sterile phenotype such as inhibition of flowering. Therefore, as an additional benefit of the present invention, there is no production and spread of pollen. The environment is protected thereby from the putative risk of dissemination of traits conferred by transgenes (e.g., like herbicide resistance) to other plant species. Furthermore, allergy sufferers are protected from aggravation of their hayfever by this blockage.

Ectopic expression of AtH1, a gene encoding a homeotic transcription factor involved in the pathway for phytochrome B signal transduction, in the dicot plants *Arabidopis* and tobacco resulted in a delayed flowering phenotype. The phenotype could be reversed to flowering by exogenous application of gibberellic acid (see Intl. Patent Appln. No. PCT/IB98/00821 published as WO 98/51800).

In contrast, the mechanism that controls the transition to flowering in grasses is currently unknown and persons skilled in the art had no reasonable expectation that the function of the AtH1 gene would be conserved in monocot species. Thus, the inhibition of flowering in grasses and the switch from vegetative to generative growth, instead of mere delay in flowering, was unexpected.

SUMMARY OF THE INVENTION

The present invention broadly encompasses a genetically modified grass in which generative propagation is inhibited or substantially reduced. Such inhibition is at least "substantial" in that there is a dramatic reduction in a phenotype (i.e., change in one or more plant characteristics resulting from the genetic modification) as compared to the same species that has not been genetically modified. More specifically, it is directed to a non-flowering grass. The plant may be male sterile or female sterile. Even more specifically, the genetic modification may interfere with metabolism of gibberellic acid (e.g., by ectopic expression of a homeobox gene encoding a transcription factor, in particular a transcription factor that blocks heading). Vegetative growth may be increased thereby. Thus, the digestibility and/or nutritional value of animal feedstuff may be improved.

Moreover, the present invention encompasses seed and other plant parts (e.g., pollen or ovum forming), at least some of which may be used for sexual or asexual propagation of the grass. The present invention may be used for forage or amenity purposes. Exemplary species useful for the present invention are of *Dactylis glomerata* L., *Festuca arundinacea* schreb., *Festuca pratensis* huds., *Lolium perenne* L., *Lolium multiflorum* lam., *Phleum pratense* L., *Agrostis tenuis* sibth., *Festuca rubra* L., *Festuca ovina* ssp. Duriuscula (L.) koch, *Poa pratensis* L., *Poa trivialis* L., *Medicago saliva* L., *Trifolium pratense* L., *Trifolium repens* L., *Agrostis* L. Bermuda, *Agrostis tenuis*, and *Agrostis stolonifera*.

In addition, the present invention teaches methods of making and using such genetically modified grasses. The genetic modification of the grass may be produced by transformation of a grass species with a nucleic acid. For example, the nucleic acid may interfere with metabolism of gibberellic acid. This nucleic acid can come from a monocot or dicot. The nucleic acid may express a gene encoding for a transcription factor (e.g., the homeobox gene AtH1 which can be derived from *Arabidopsis* or other equivalents thereof).

The phrase "ectoptic expression" is defined as expression of a gene at a time and/or in an amount that is different from the endogenous gene activity and sufficient to confer the desired phenotype.

Optionally, the same or another nucleic acid may be introduced to confer another linked or unlinked heritable trait (e.g., herbicide or pest resistance).

The genetically modified grass may be grown and/or propagated. It may be used for athletic fields, lawns, parks, and other types of landscaping (i.e., amenity uses). For example, sports such as baseball, cricket, football, golf, rugby, soccer, and tennis may be played on grass of the present invention. Animals such as livestock (e.g., cattle, goats, horses, sheep) may graze directly thereon or eat feed processed from the genetically modified grass (i.e., forage uses). The invention provides a more digestible feedstuff for ruminant animals than the parental flowering grass even after extensive cuttings.

The genetic modification may result in a heritable change in one or more plant characteristics such as, for example, inhibition of flowering (or substantial delay that amounts to inhibition), absence of inflorescence, increased production of tillers, delayed heading, and inhibition of the developmental switch from vegetative to generative growth.

It would be useful to be able to relieve or reverse one or more such changes. For example, expression of a gene may be normalized or a phytohormone may be applied to the grass to restore gibberellic acid metabolism. The phytohormone may be a gibberellin compound in its acid or salt, ether or ester forms; it may be formulated with a carrier that enhances penetration (e.g., dimethyl sulfoxide, alcohol, surfactant). A switch to generative propagation may be induced by genetic or chemical methods.

Another aspect of the invention is related to preventing the escape and/or spread in the environment of one or more other plant characteristics (e.g., herbicide or pest resistance) that have also been genetically engineered as a trait. Thus, the putative risk associated with the spread of genetically engineered traits to non-modified plant relatives is minimised.

DESCRIPTION OF THE INVENTION

Figure 1:
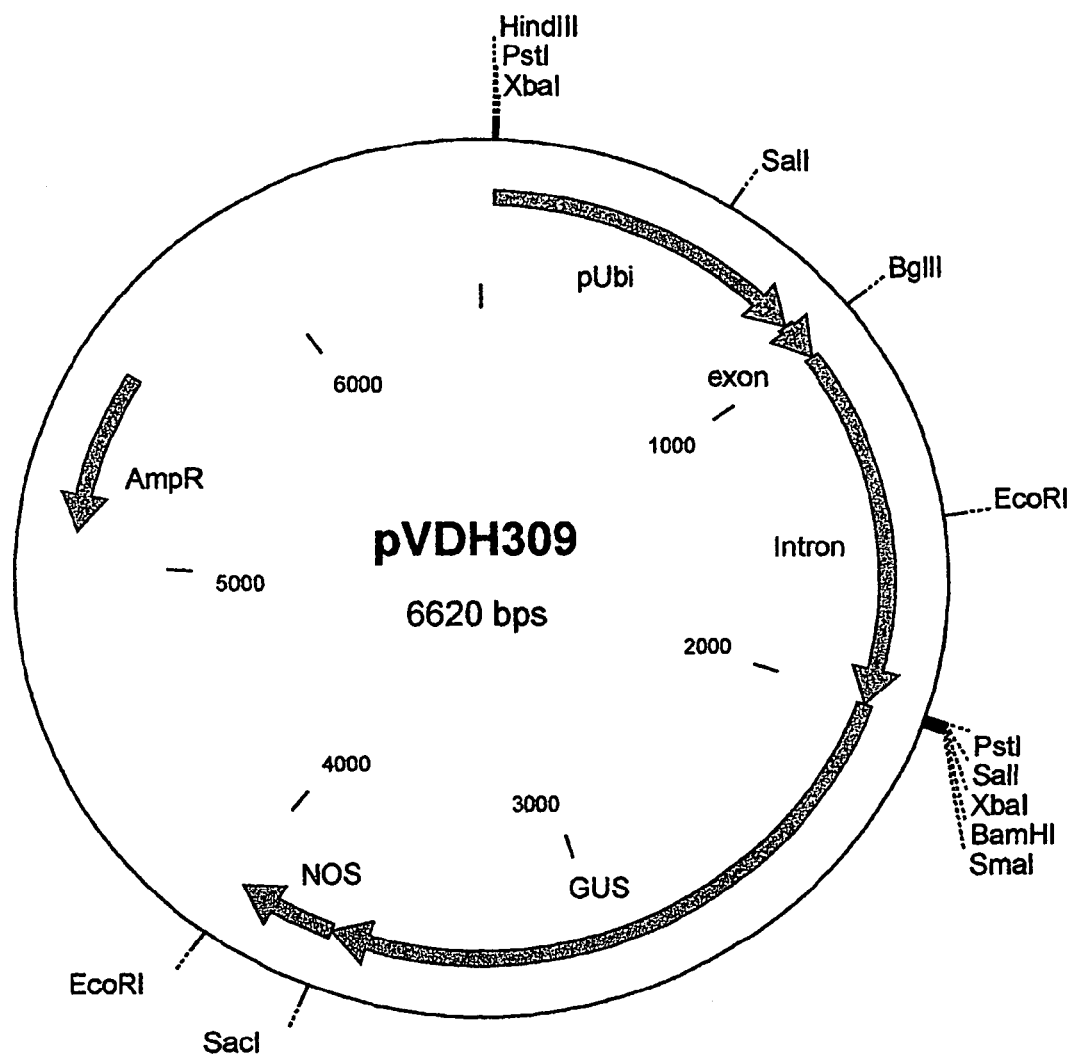
FIG. 1 shows a physical map of pVDH309.

This invention describes a method to inhibit generative propagation in grass. It can be used to block the transition to flowering in grasses, as well as to control the process to switch back to flowering when this is desired.

This technology is useful in all grass species. They all have different primary uses, but the non-flowering technology is beneficial for agricultural use such as in alfalfa or in other forage grasses. In amenity grasses, non-flowering increases visual uniformity of the grass top and increases the lush bushiness of the lawn. Hardiness and ease of maintenance are plant characteristics desirable for areas that receive heavy use such as, for example, publicly accessible areas like parks and athletic fields.

TABLE 1

Grasses for which the invention is particularly useful.

| | |
|---|---|
| *Dactylis glomerata* L. | Cocksfoot |
| *Festuca arundinacea* schreb. | Tall fescue |
| *Festuca pratensis* huds. | Meadow fescue |
| *Lolium perenne* L. | Perennial ryegrass |
| *Lolium multiflorum* lam. | Italian ryegrass |
| *Lolium multiflorum* lam. | Westerwold ryegrass |
| *Phleum pratense* L. | Timothy |
| *Agrostis tenuis* sibth. | Browntop |
| *Festuca rubra* L. | Chewings fescue |
| *Festuca rubra* L. | Slender creeping red fescue |
| *Festuca rubra* L. | Creeping fescue |
| *Festuca ovina* ssp. Duriuscula (L.) koch | Hard fescue |
| *Poa pratensis* L. | Smooth-stalked meadowgrass |
| *Poa trivialis* L. | Rough-stalked meadowgrass |
| *Medicago sativa* L. | Lucerne |
| *Trifolium pratense* L. | Red clover |
| *Trifolium repens* L. | White clover |
| *Agrostis* L. Bermuda | Bent grass |
| *Agrostis tenuis* | Browntop bent |
| *Agrostis stolonifera* | Creeping bent |

The term "grass" as used herein refers to those listed in Table 1 and other monocots commonly considered grass but not including those monocots commonly considered cereals such as corn, rice, wheat, barley, and the like.

Turfgrass seed must be evaluated for the suitability of different cultivars for various amenity uses. There are a number of institutes that test grasses for various uses. Most of the sports-type uses require high levels of wear tolerance and shoot density. The invention avoids generative growth and, thus, only exhibits vegetative growth under usual conditions. This vegetative growth results in more shoot density and more wear tolerance. The combination of a cultivar that has been bred to have excellent levels of shoot density and wear tolerance with this genetic modification is very promising for recreational and sports uses. Of particular interest are certain cultivars that are presently marketed in the U.K. such as Master perennial ryegrass for soccer and rugby pitches and Amadeus (*Lolium perenne*) for cricket fields and lawns.

Grass cultivars are ranked according to different sets of criteria by the Sports Turf Research Institute (STRI) in England. For winter pitches the criteria produced by the STRI is based on mean wear tolerance over low and high fertiliser inputs, and shoot density. These characteristics are important for sports pitches receiving intensive wear such as soccer and rugby pitches. The invention increases the shoot density and thus results in a grass that is superior for sports uses.

The invention can be employed in a number of grass types allowing the effect of enhanced vegetative growth and tillering to be used in a number of applications. When employed in a finer leafed grass the invention is highly useful for lawns, parks, general landscaping, and ahtletic fields. Perennial ryegrass (*Lolium perenne*) is tested by STRI for tolerance of close mowing, shoot density, fineness of leaf, slow regrowth (regular mowing), mean, cleanness of cut, short growth (infrequent mowing), freedom from red thread, summer greenness and winter greenness. The invention is particularly useful when introduced into cultivars such as Bellevue which already evidence traits such as enhanced shoot density, fineness of leaf, and tolerance to close mowing.

Cultivars of Chewings fescue and slender creeping red fescue are suitable for use in very close mown turf (for example golf and bowling green mown at 5 mm) and for more general uses such as lawns and golf fairways. For general turf, the cultivars are looked at for shoot density and tolerance to close mowing. Tolerance of close mowing and shoot density will be of most importance for ornamental lawns and very close mown turf such as golf and bowling greens. The invention will enhance shoot density of Chewings fescue and slender creeping red fescue, and render them suitable for this type of use.

Cultivars of browntop bent (*Agrostis tenuis*) and creeping bent (*Agrostis stolonifera*) are used in golf and bowling greens which are closely mown, and for ornamental lawns and golf fairways. Velvet bentgrass is a dense turf and exhibits some drought tolerance. However, it also produces more thatch than other bentgrass species. When genetically modified to inhibit generative propagation and optionally to be herbicide resistant, grass with vegetative-only growth would enhance its useful for greens and fairways. Additionally, it may reduce mowing costs associated with removal of seed heads of the grass. Thus, grasses of the Invention may also be aesthetically more pleasing to the eye than grasses which have flowered.

Smooth-stalked meadowgrass (*Poa pratensis*) for use in winter pitches (soccer, rugby, etc.) is tested by STRI for wear tolerance, shoot density, fineness of leaf, slow regrowth (regular mowing), freedom from leaf spot, orange stripe rust resistance, summer greenness and winter greenness. Such plant characteristics are clearly of importance for amenity uses. Therefore, the invention can be used for landscaping and sports either in combination with the naturally high levels of shoot density or to increase the shoot density of cultivars lacking such a trait.

Cultivars of smooth-stalked meadowgrass (*Poa pratensis*) can be employed under football-type wear for inclusion in winter pitches and for landscaping (e.g., lawns and parks). Smooth-stalked meadowgrass is tested by STRI on tolerance of shoot density, fineness of leaf, mean, slow regrowth (regular mowing), short growth (infrequent mowing), freedom from leaf spot, orange stripe rust resistance, summer greenness, and winter greenness. Once established, smooth-stalked meadowgrass can be useful for football (soccer) wear and has tolerance of close mowing. However, establishment of this grass is slow and results cannot be achieved until at least 12 months after sowing. The invention may enhance the establishment of the grass and reduce the down time prior to use.

U.S. golf courses frequently employ *Agrostis* L. (bent grasses) while golf courses in Europe employ the fine tillered meadow fecsue. The soccer fields of Europe frequently employ mixtures of *Lolium perenne* and *Poa* grasses. All of these grass uses are improved by the use of a non-flowering grass. Non-flowering grass increases the longevity under wearing conditions of the grass due to the bushiness resulting from the plant placing energy into the production of tillers instead of the production of inflorescence. Additionally, these additional tillers create a more level cut grass surface, (a uniform sward) which may enhance ball directional control in golf for example. The increased vegetative growth should reduce brown spots due to cleat or divot damage. Additionally, the use of a non-flowering herbicide resistance grass is particularly useful to decrease care and maintenance costs associated with the removal of weeds from greens, pitches and fairways and roughs.

The invention can be introduced into other plants by conventional breeding methods such as forming hybrids, conventional breeding, backcrossing, or cross pollination, (after the non-flowering is switched off by application of a phytohormone which induces flowering). Or alternatively, the invention can be introduced into a grass by genetic modification of the plant. This transition to non-flowering can be through introduction of genetic material (e.g., a nucleic acid like an expression vector) by transformation processes.

Transition to flowering in a plant is a critical and complex developmental process during the life cycle of a plant. The process is controlled by external factors like day length, light quality and quantity, low temperature, availability of water and nutrients. Moreover, internal factors like plant size, and number of internodes are considered to be critical. The plant senses this complex array of environmental cues and this information is relayed to the nucleus where the gene expression profile is modulated in order to respond appropriately to the existing conditions. This mechanism maximises the chances of a plant to successfully produce viable offspring and therefor contributes to its fitness.

These properties, which increase the survival rate in nature of the plant species, can be in conflict with the characteristics desired for agricultural use. Transition to flowering in grasses is a trait, which lowers the benefits of this crop-group for agricultural use. However, for seed production, one of the objectives of grass breeding is to select for varieties which are good flowering. However now that there is the present invention an objective of grass breeding can include selection of varieties which are delayed or completely blocked in the switch to flowering. A prerequisite for grass seed production (but not for sod production) is to design a controlled switch mechanism which allows seed production when required.

The regulation of the flowering induction process is under control of a large number of gene loci. Molecular genetic studies on *Arabidopsis* currently have identified a total number of 80 loci involved in the control of flowering time. This complexity combined with the diversity which exist between plant species with respect to the flowering induction process make it hard to predict which gene products are key regulatory factors in the signal transduction cascades that control the transition to flowering. As a consequence, the efficacy of exploiting available genetic factors in either homologous or heterologous systems with the objective to control the developmental regulation cannot be predicted on theoretical grounds but needs to be tested experimentally case by case.

In WO 98/51800, the use has been described of a homeotic gene called AtH1 derived from the dicotyledonous plant species *Arabidopsis thaliana* to control the flowering induction process. Ectopic overexpression of the Ath1 gene in dicots like *Arabidopsis* and tobacco significantly inhibited the transition to flowering, whereas downregulation of this gene in *Arabidopsis* resulted in precocious flowering. Biochemical analysis showed that overexpression of the AtH1 gene in tobacco lowers the endogenous concentration of biological active forms of the phytohormone gibberellic acid. The inhibited flowering phenotype can be reversed by exogenous application of gibberellic acid:

A number of formulations containing a gibberellin compound in various forms such as ethers, esters, salts or acids could be used to induce flowering. Exemplary compounds are GA3 or 16,17-dihydro-GA3 or 3-epi-GA3 or 3-epi-16, 17-dihydro-GA3 or 2,2-dimethyl-GA4 and its $3\alpha$-OH derivative and its 16,17-dihydro derivative and 3-epi-2,2-dimethyl-GA4 and its 16,17-dihydro derivative and GA5 and its 16,17-dihydro derivative and $15\beta$-OH-GA5 and its 16,17-dihydro derivative including exo-16,17-dihydro -GA$_5$. Other examples include exo-16,17-dihydro-GA5, endo-16,17-dihydro-GA5, exo-16,17-dihydro-GA5-13-acetate, endo-16,17-dihydro-GA5-13-acetate, exo-16,17-dihydro-GA5-13-n-propyl ether.

The invention describes the use of the AtH1 gene in monocotyledonous plant species like grasses with the objective to control the flowering induction process. Transition to flowering in grasses is characterised by a three-month vernalisation requirement and consecutive long day conditions. This differs from the *Arabidopsis* and tobacco varieties used earlier to demonstrate the efficacy of AtH1 to control flowering induction which do not require vernalisation and are day-length independent. Therefor it could not be predicted and it was surprising that ectopic expression of AtH1 in transgenic grasses would result in a delayed and/or non-flowering phenotype. The tillering evidenced by this vegetative growth in the plant and the lack of any negative phenotype changes such as dwarfism or other abnormalities was very surprising.

Initially it was believed that a monocot homologue of the AtH1 gene would have to be found. It is still believed that this would be a usefully homologue as would most of the other monocots homologues from corn, lilies, rice, wheat and the like. But just as a inexpensive test, which was not expected to work, a DNA construct using the dicot gene was made. It was not evident that this dicot gene would be useful in a monocot. However, upon expression in of the dicot AtH1 gene the transgenic grass plants showed an accumulation of the AtH1 protein which then might inhibit the flowering induction process.

The vector used to transform grass is based on pBluescript and contains the AtH1 cDNA under transcriptional control of the ubiquitin promoter derived from maize. This promoter is constitutively active in monocotyledonous species including Grass and is therefor useful to overexpress transgenes. Additionally, it is noted that promoters that are triggered to stop in the presence of the gibberellic acid are very useful. However, other promoters can be useful in this respect as well. Possibly tissue-specific promoters like promoters exclusively active in shoot apical meristem could also be used.

In order to select for transformants use is made of a HPTII gene, which upon expression confers resistance towards the antibiotic hygromycin. Hygromycin has been shown to be very effective as a selective agent but other selectable marker systems could be used as well like kanamycin resistance, glyphosate resistance, gluphosinate-ammonium resistance, and the like. In order to generate transgenic *Lolium* plants embryogenic suspension cultures were bombarded using the so-called particle inflow gun (PIG). Other transformation systems can be used as well like the whisker system or *Agrobacterium tumefaciens*. The transformation experiments have resulted in a large number of hygromycin resistant, transgenic *Lolium* plants, which were characterized molecularly. The number of integrated copies of the AtH1 construct was variable and ranged from one to ten.

The transformants were analysed further by RT-PCR in order to select those transformants that express the integrated AtH1 gene. AtH1 mRNA could be detected in about 70% of the transformants. A group of control non-transformed plants as well as the transgenic plants were used in a flowering experiment. In order to do this the plants were vernalised for 10 weeks at an average temperature of 4° C. After the vernalisation period, the plants were placed under conditions favoring induction of flowering (i.e., long days of 16 hr light/8 hr dark) and 20° C. Plants were monitored weekly for the appearance of inflorescences. Control non-transformed plants, which share the same genetic background as the transformant plants, were developing inflorescences about three to six weeks after transfer to long day conditions (99% of the individual plants). However, a significant number (i.e., 18%) of AtH1 expressing, independent transformants did not flower at all even at four months after transfer to long days. This result shows that, surprisingly, ectopic expression of the Ath1 gene in transgenic grass can result in a complete block of the transition to flowering. Moreover, the non-flowering transformants continued developing vegetatively which resulted in a large increase of biomass. No obvious negative pleiotropic effects were observed for the non-flowering transformants.

In agronomic practice, fields are treated with phytotoxic, chemical compounds to control weeds. If these compounds are applied during the life cycle of the crop, the crop needs to be resistant to the compound. One way to confer resistance to the otherwise susceptible crop is to transgenically introduce a resistance gene into the crop. In order to have a sustainable system of susceptible weeds and a tolerant crop it is pertinent that the resistance gene does not flow into the germplasm of the weedy relatives of the crop. This is especially an issue in cultivated grass crops, which have many wild relatives with which genetic material can be exchanged. A strategy to prevent the flow of genetic resistance traits from a cultivated crop into its wild and weedy relatives is disclosed: a non-flowering genetic trait is combined with a gene conferring resistance to the phytotoxic compound. Although not used as such in agronomic practice, hygromycin is a phytotoxic compound. Grass plants treated with hygromycin in vitro die, unless they express the HPTII resistance gene.

The invention demonstrates that plants inhibited for generative propagation as well as containing a transgene conferring resistance to a phytotoxic compound like hygromycin survive treatment with the phytotoxic compound, whereas control plants not expressing the transgene conferring hygromycin resistance do not. This demonstrates that a genetic trait linked to a non-flowering gene can be used in vivo and that the non-flowering technology is useful to lower the risk of the spreading of transgenes in the environment.

A normally flowering grass can be genetically modified by a transformation method such as a gun apparatus, an inflow apparatus (PIG), or an *Agrobacterium* which is adapted for monocot use. The transformation method must be capable of the introduction of a functional gene construct. This gene construct should lead to the biosynthesis and accumulation of a homeotic protein. The specific homeotic protein or functional homologues (a functional homologue protein is a protein that results in a novel and unexpected life cycle of the grass plant characterized by an extended vegetative growth phase and inhibited generative growth phase) of that protein AtH1 originating from the cruciferous plant species *Arabidopsis thaliana* results in a novel and unexpected life cycle of the grass plant characterized by an extended vegetative-growth phase and as a consequence a significant increase in yield of biomass. This biomass is containing substantially more digestible feedstuff for ruminant animals than the flowering control grass even after extensive numbers of grass cuttings.

Plants made in accordance with the invention were demonstrated to continue developing in a vegetative mode despite their being subjected to environmental conditions strongly favoring the phase transition to flowering for non-transformed control plants having the same genetic background. A plant characteristic conferred by the invention can be at least partially relieved or reversed by application of a phytohormone (e.g., a gibberellin compound).

The invention is further described by the following examples, but its practice is not limited thereby.

EXAMPLES

Example 1

Preparation of Transformation Vectors

In order to obtain transgenic grasses expressing the AtH1 gene derived from *A. thaliana* (Quaedvlieg et al., 1995), an expression vector was made which contains the AtH1 cDNA under the transcriptional control of a promoter derived from the ubiquitin (UBI) gene from maize (Christensen et al., 1992), including the first exon-intron combination in order to enhance expression. The polyadenylation signal derived from the nopaline synthase gene (Tnos) of *Agrobacterium tumefaciens* was attached at the 3'-end of the cDNA to allow proper termination of transcription. Covalently linked to the chimeric AtH1 gene was a selectable marker comprised of the actin promoter (ACT) derived from rice, the HPTII gene derived from *Escherichia coli*, and the 35S polyadenylation signal (T35S) derived from Cauliflower Mosaic Virus (McElroy et al., 1991; Spangenberg et al., 1995a). Expression of the selectable marker confers-resistance to the antibiotic hygromycin, which can be used to select transformed plants.

Figure 2:
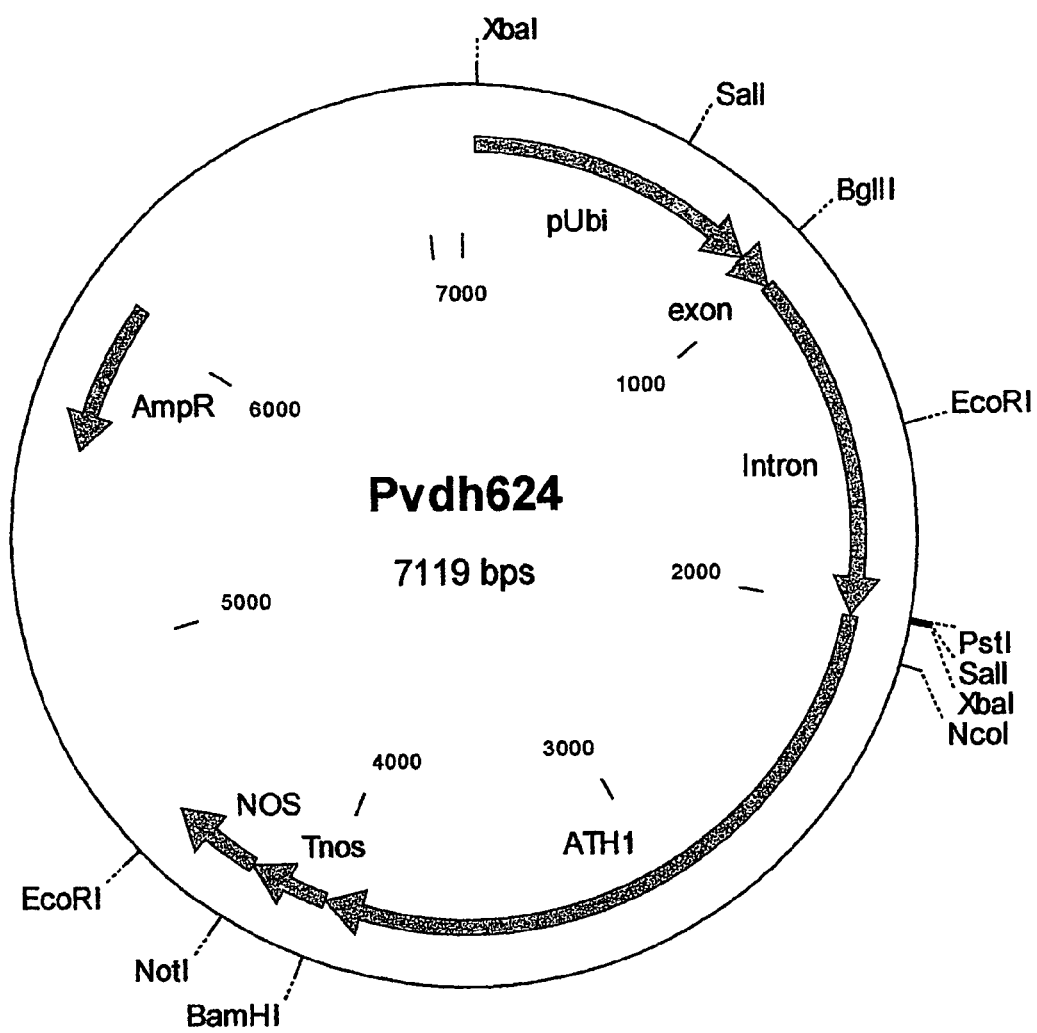
FIG. 2 shows a physical map of pVDH624.
Figure 5A:
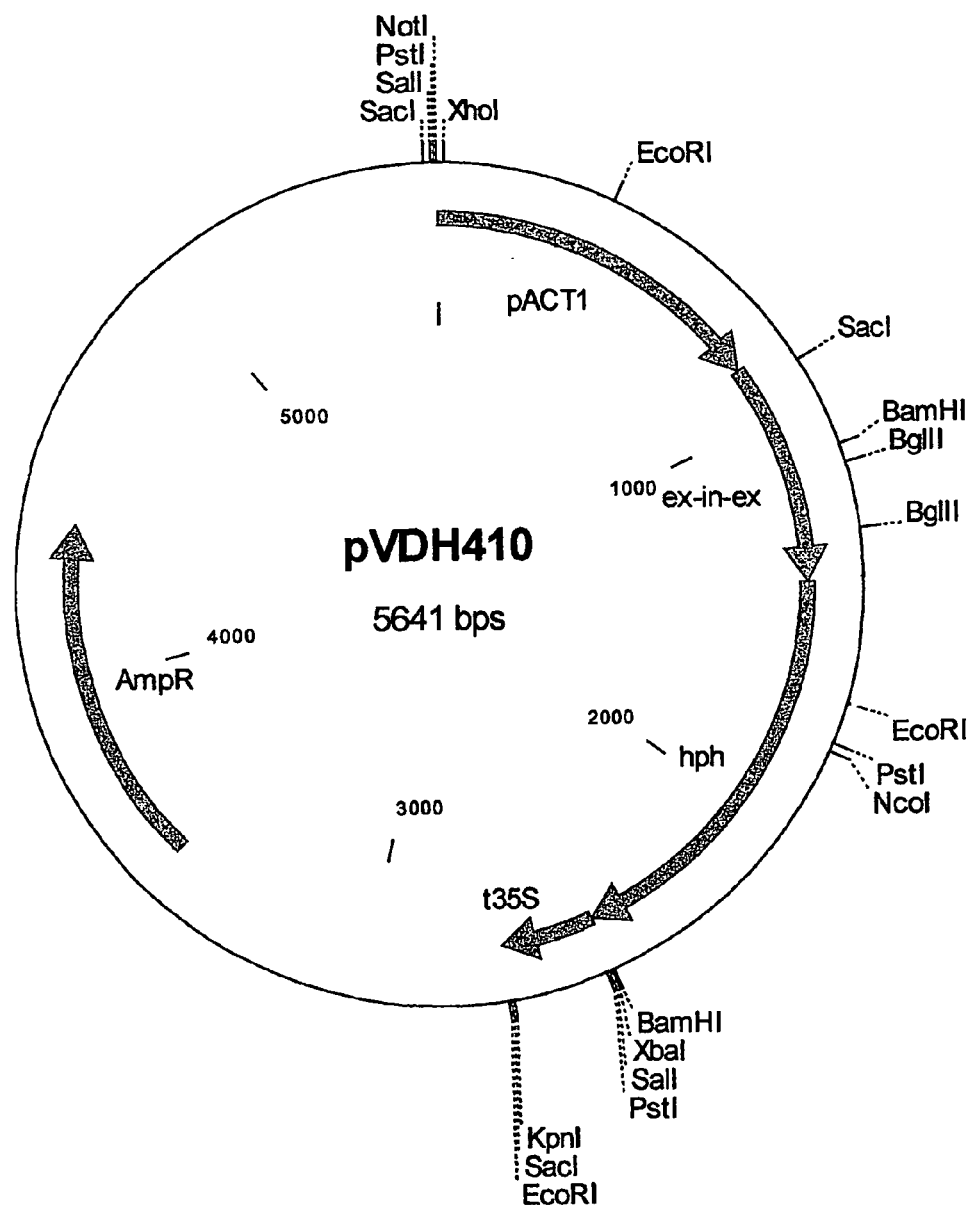
FIG. 5A shows a physical map of pVDH410.
Figure 5B:
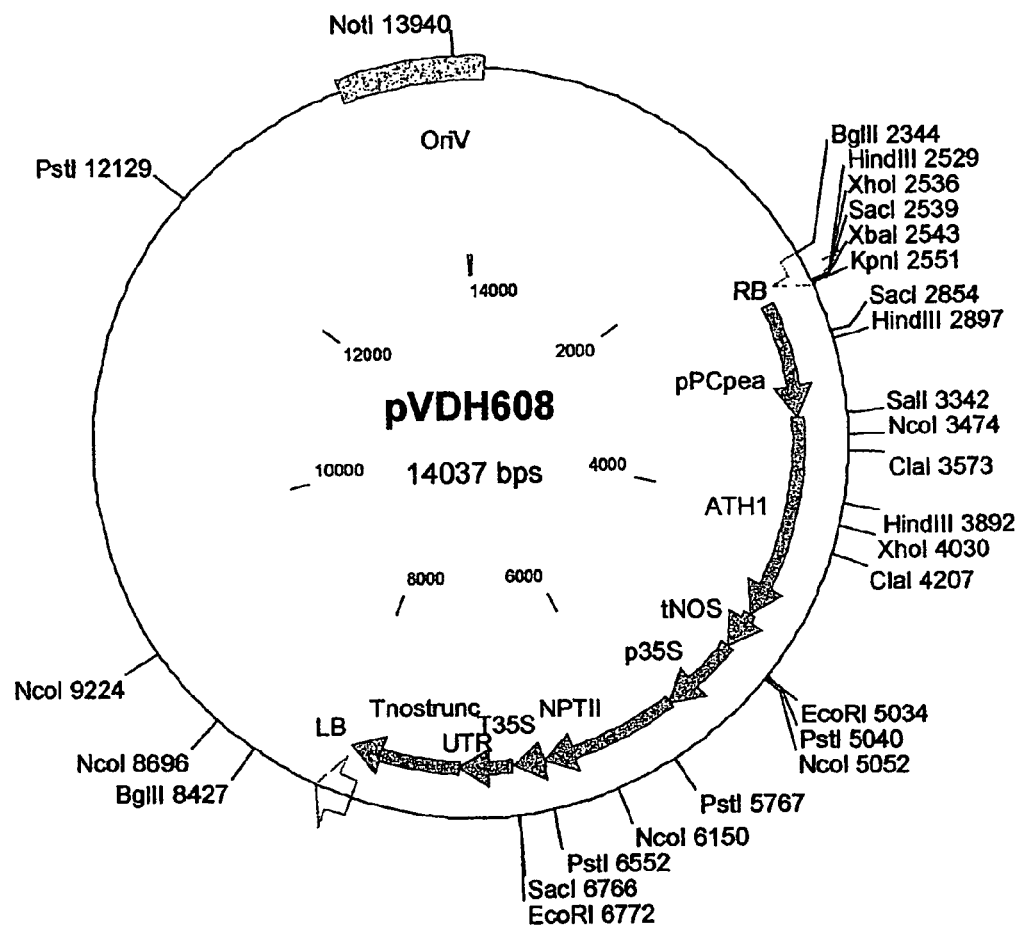
FIG. 5B shows a physical map of pVDH608.
Figure 5C:
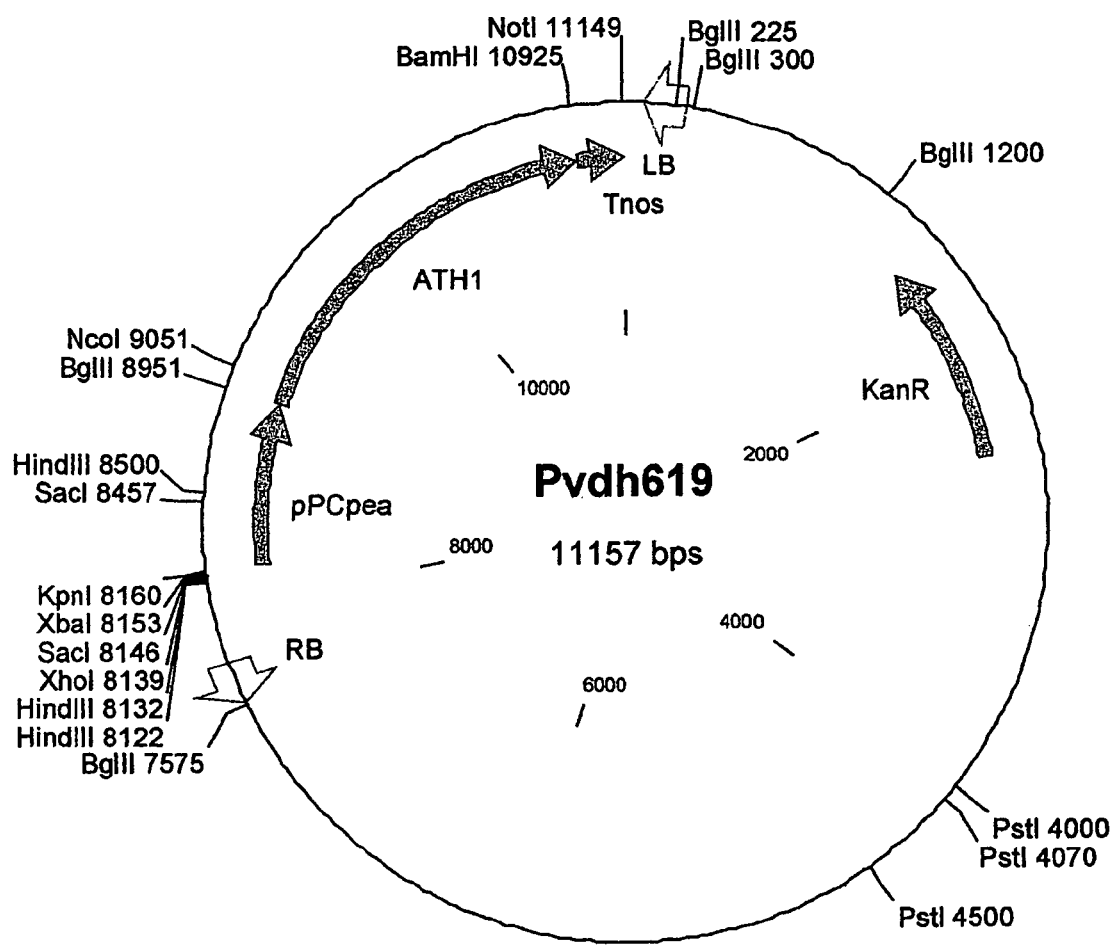
FIG. 5C shows a physical map of pVDH619.

The construct was made using standard molecular cloning techniques and protocols well known to the person skilled in the art. In detail the construct was made according to the following steps. The SacI site of the plasmid pVDH309 (FIG. 1), containing the UBI-promoter linked to a gene encoding beta-glucuronidase (GUS), was made blunt by T4 DNA polymerase after which a NotI linker was attached to it. The resulting plasmid, called pVDH527, was digested with BamHI and NotI which removed the GUS-gene which was subsequently replaced by a full length AtH1 cDNA with a Tnos attached to the 3'-end which was released from plasmid pVDH619 (FIG. 5C) after digestion with Bg/II and NotI. The resulting plasmid is called pVDH624 (FIG. 2).

Figure 3:
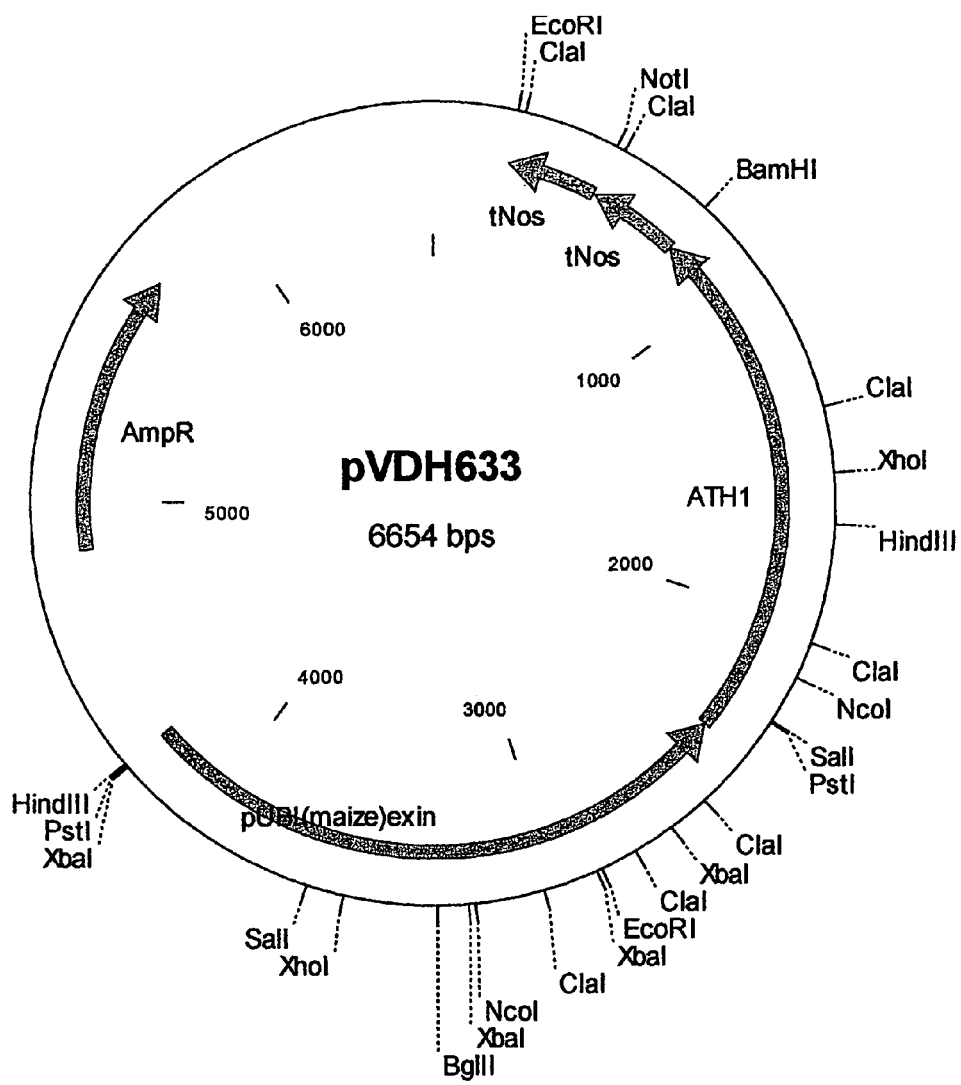
FIG. 3 shows a physical map of pVDH633.
Figure 5D:
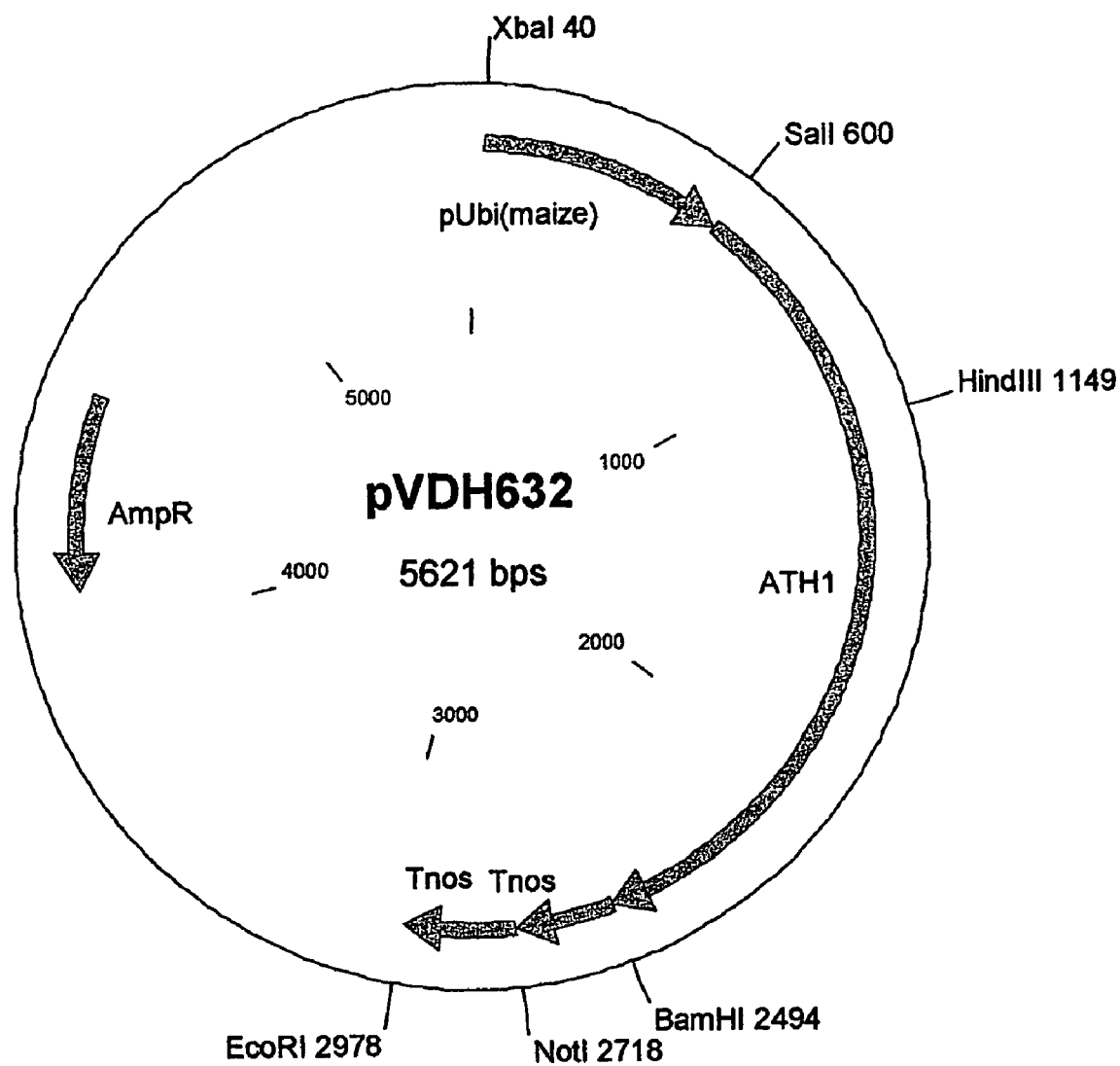
FIG. 5D shows a physical map of pVDH632.

The primary structure of the UBI-AtHI construct was analysed by sequencing, which revealed a frame-shift mutation in the open reading frame of the AtH1 gene. To repair this mutation, a novel AtH1 cDNA was prepared by PCR using a plasmid called pVDH608 (FIG. 5B) as template, which contained a correct version of the AtH1 cDNA. As the forward primer 5'-GCG TCG ACC CM TGG ACA ACA ACA ACA ACA AC-3' (SEQ ID NO:3) and as the reverse primer 5'-GCG GAT CCG AGT AGC MT TGC CTA ATT ATC AC-3' (SEQ ID NO:4) were used. The PCR-product was digested with Sa/I and BamHI to generate sticky ends and ligated into pVDH624 digested with Sa/I and BamHI, which resulted in plasmid pVDH632 (FIG. 5D). As the UBI-promoter also contains a Sa/I site, the Sa/I fragment of the UBI-promoter had to be introduced into pVDH632 in order to obtain the appropriate UBI-AtHI construct called pVDH633 (FIG. 3).

Figure 4:
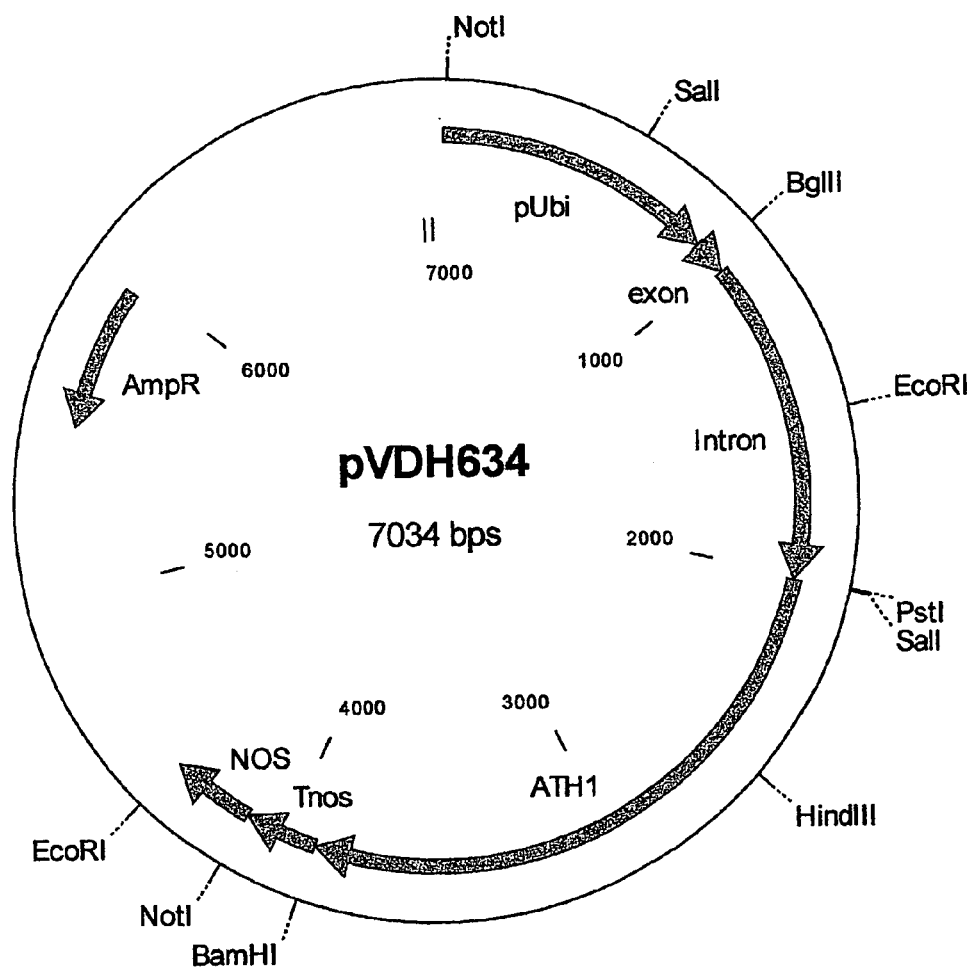
FIG. 4 shows a physical map of pVDH634.
Figure 6:
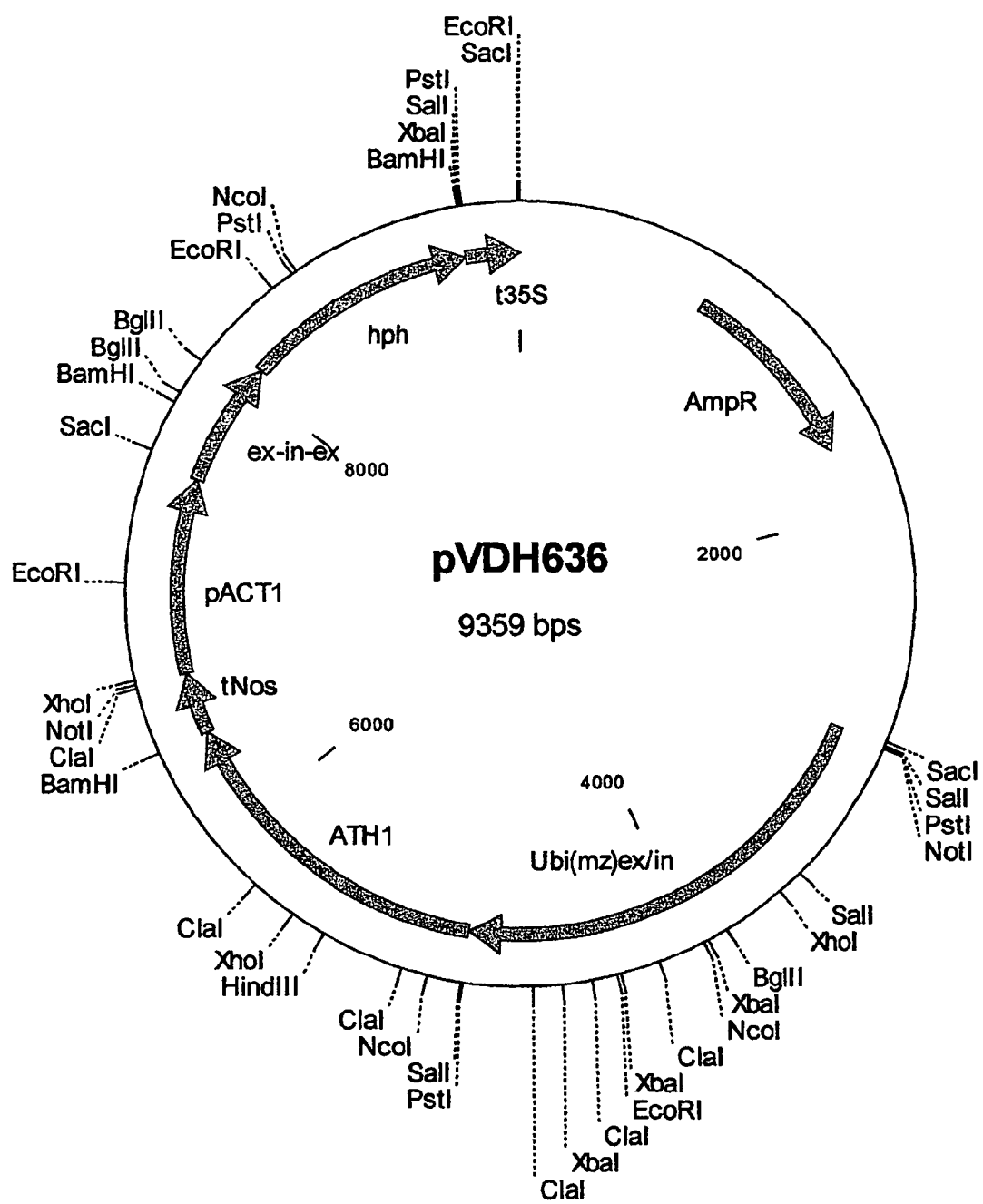
FIG. 6 shows a physical map of pVDH636, its nucleotide sequence (SEQ ID NO:1), the molecular features of pVDH636, and the predicted amino acid sequence (SEQ ID NO:2) of AtH1.

The XbaI site locate at the 5'-end of the UBI-promoter was modified to a NotI site by filling in the digested XbaI site with Klenow polymerase and ligating a NotI linker to the blunt end. The resulting plasmid is called pVDH634, which is shown in FIG. 4. Sequence analysis showed this UBI-AtHI construct to be correct. The plasmid pVDH634 was subsequently digested with NotI, which released the complete UBI-AtHI-NOS chimeric gene. This DNA fragment was inserted into the NotI site of the plasmid pVDH410 (FIG. 5) which is a pUC-derived plasmid containing the ACT-HPTII selectable marker with a unique NotI site at its 5'-end. The resulting vector, which contained both genes in the same transcriptional orientation, was called pVDH636 (FIG. 6) and was used in *Lolium* transformation experiments using the particle inflow gun as DNA delivery system. The integrity of the plasmid was confirmed by sequence analysis. The complete primary structure of pVDH636 is shown in FIG. 6. In addition, transformation was carried out using a mixture of the vectors pVDH410 and pVDH633.

Example 2

Transformation of *Lolium perenne*

Embryogenic suspension cultures of *Lolium perenne* L. (cv. Mondial) were established (Spangenberg et al., 1995a) and transformed with pVDH636, using the particle inflow gun (PIG) (Finer et al., 1992). Filters with an embryogenic suspension culture were bombarded with gold particles coated with the transformation vectors. Transformed tissues were selected using hygromycin B according to Spangenberg et al. (1995b). The results of the transformation using pVDH636 are shown below.

TABLE 2

Summary of *Lolium* transformations using pVDH636

| Plasmid | # filters bombarded | # filters with hyg$^R$ shoots | # transformants | Minimum # of independent transformants |
|---|---|---|---|---|
| pVDH636 | 787 | 306 | 943 | 279 |

As can be seen from the results shown in Table 2, approximately 39% of the filters carrying the embryogenic suspension cultures ultimately resulted in hygromycin resistant shoots. After transfer to rooting medium, a total number of 943 putative transformants were obtained. However, as individual plants which are derived from one and the same filter are considered to be possibly dependent (i.e. genetically identical), the total number of independent transformants as defined as the number of hygromycin resistant plants regenerated from different filters was 279.

In a separate transformation experiment co-bombardment of a mixture of two transformation vectors was carried out. This allows genetic segregation between the integrated ACT-HPTII construct and the integrated UBI-AtH1 construct in offspring for those events in which the two integrated plasmids are not genetically linked. The two vectors used for this transformation experiment were pVDH410, which contains the ACT-HPTII selectable marker, and pVDH633, which contains the UBI-AtH1 construct. The results of the transformation using pVDH410 and pVDH636 are shown below.

TABLE 3

Summary of *Lolium* transformations using pVDH410 and pVDH636

| Plasmids | # filters bombarded | # filters with hyg$^R$ shoots | # transformants | Minimum # of independent transformants |
|---|---|---|---|---|
| pVDH410 + pVDH633 | 257 | 107 | 129 | 67 |

As can be seen from the results shown in Table 3, approximately 42% of the filters carrying the embryogenic suspension cultures ultimately resulted in hygromycin resistant shoots. After transfer to rooting medium, a total number of 129 putative transformants were obtained. However, as individual plants which are derived from one and the same filter are considered to be possibly dependent (i.e., genetically identical), the total number of independent transformants as defined as the number of hygromycin resistant plants regenerated from different filters was 67.

Example 3

Molecular Analysis of the Putative Transformants

Figure 7:
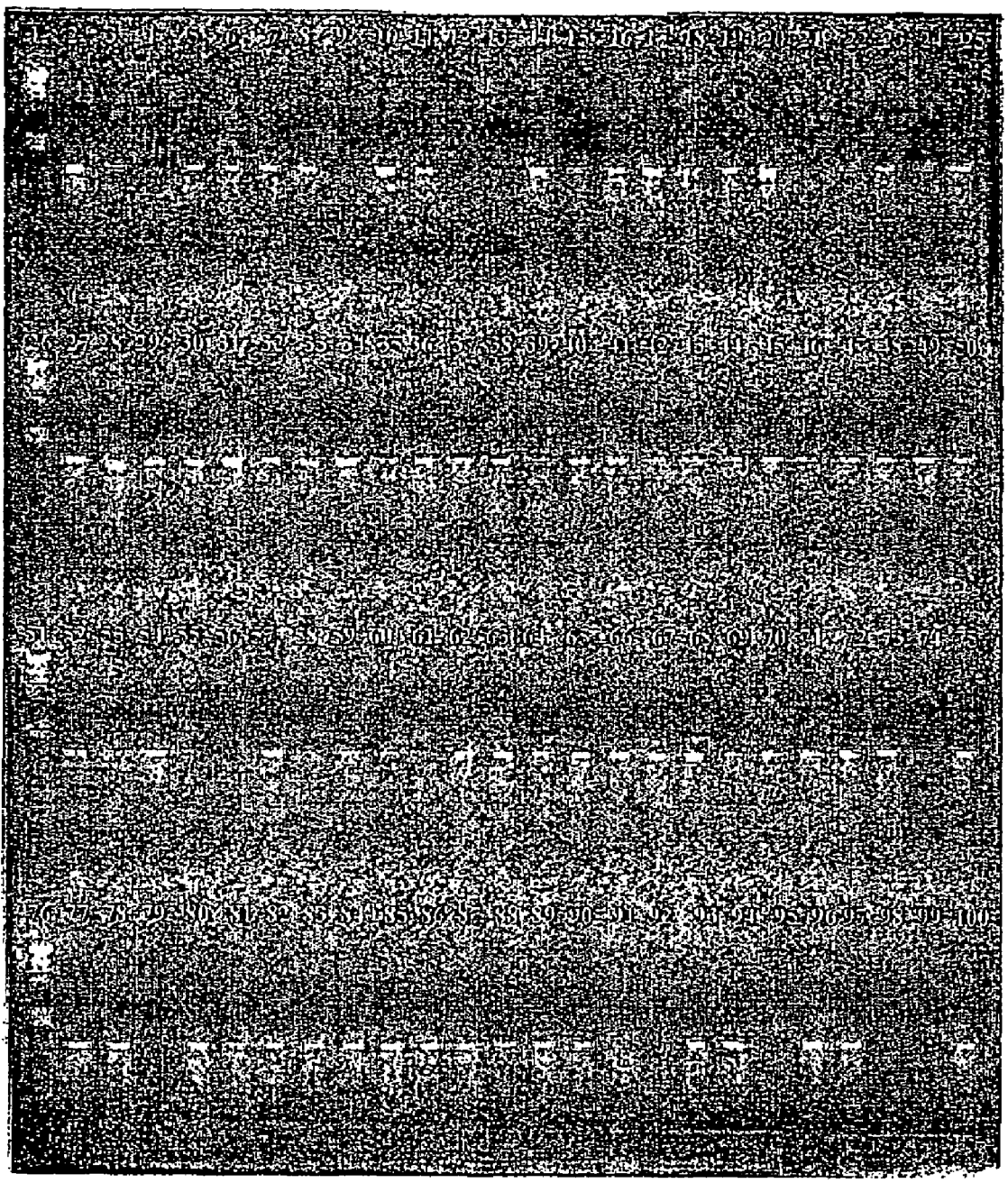
FIG. 7 shows an ethidium bromide-stained agarose gel in which bands were obtained after PCR analysis of AtH1-transformants using genomic DNA extracted from leaves. On the left-hand side of each panel (i.e., lanes 1, 26, 51 and 76), a molecular size marker (lambda DNA digested with HindIII) is shown. Remaining lanes (i.e., lanes 2-25, 27-50, 52-75 and 77-100) contain the PCR product obtained from independent transformants. Most samples analysed gave a positive PCR signal of the expected size of 1463 basepairs (bp).
Figure 8:
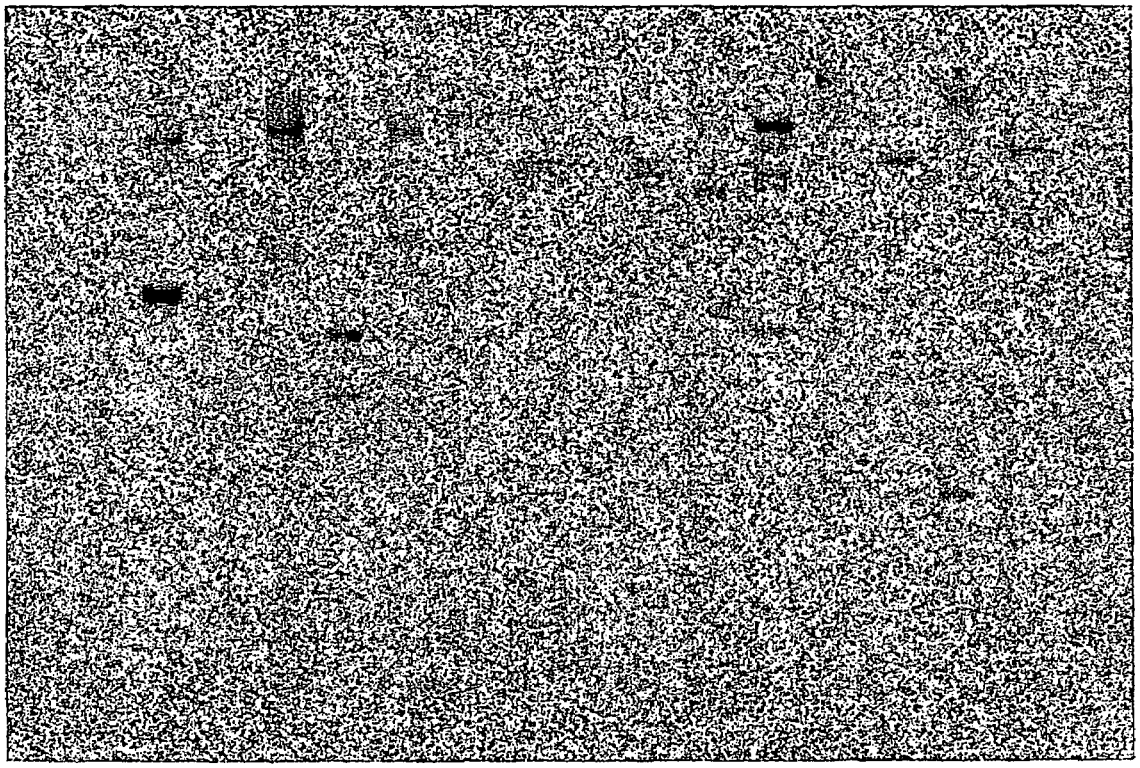
FIG. 8 shows a Southern analysis of independent AtH1-transformants of *Lolium*. Each lane contains HindIII digested genomic DNA isolated from a different, independent *Lolium* transformant. The blot was hybridised using labeled HPTII DNA as probe.

In order to select transformants, which contain a functional UBI-AtH1 construct, the hygromycin resistant plants were analysed molecularly. An initial screen was carried out by PCR to select for plants containing a minimum of one full-length copy of the AtH1 cDNA. Genomic DNA was purified from leaf explants and used in a PCR reaction containing the following primer set: forward primer 5'-GCG TCG ACC CM TGG ACA ACA ACA ACA ACA AC-3' (SEQ ID NO:3) and reverse primer 5'-GCG GAT CCG AGT AGC MT TGC CTA ATT ATC AC-3' (SEQ ID NO:4). The 1463 kb DNA fragment diagnostic for the presence of an integrated full length AtH cDNA was observed in 85% of the independent hygromycin resistant plants (FIG. 7). An estimate of the integrated number of gene copies was made by Southern analysis using the restriction enzyme HindIII to digest the genomic DNA and HPTII as a labeled probe. The result of such an analysis of plants transformed with pVDH636 is given in FIG. 8 and shows from the different banding patterns that a number of independent events have been obtained which contain estimated copy numbers ranging from one to ten.

Figure 9:
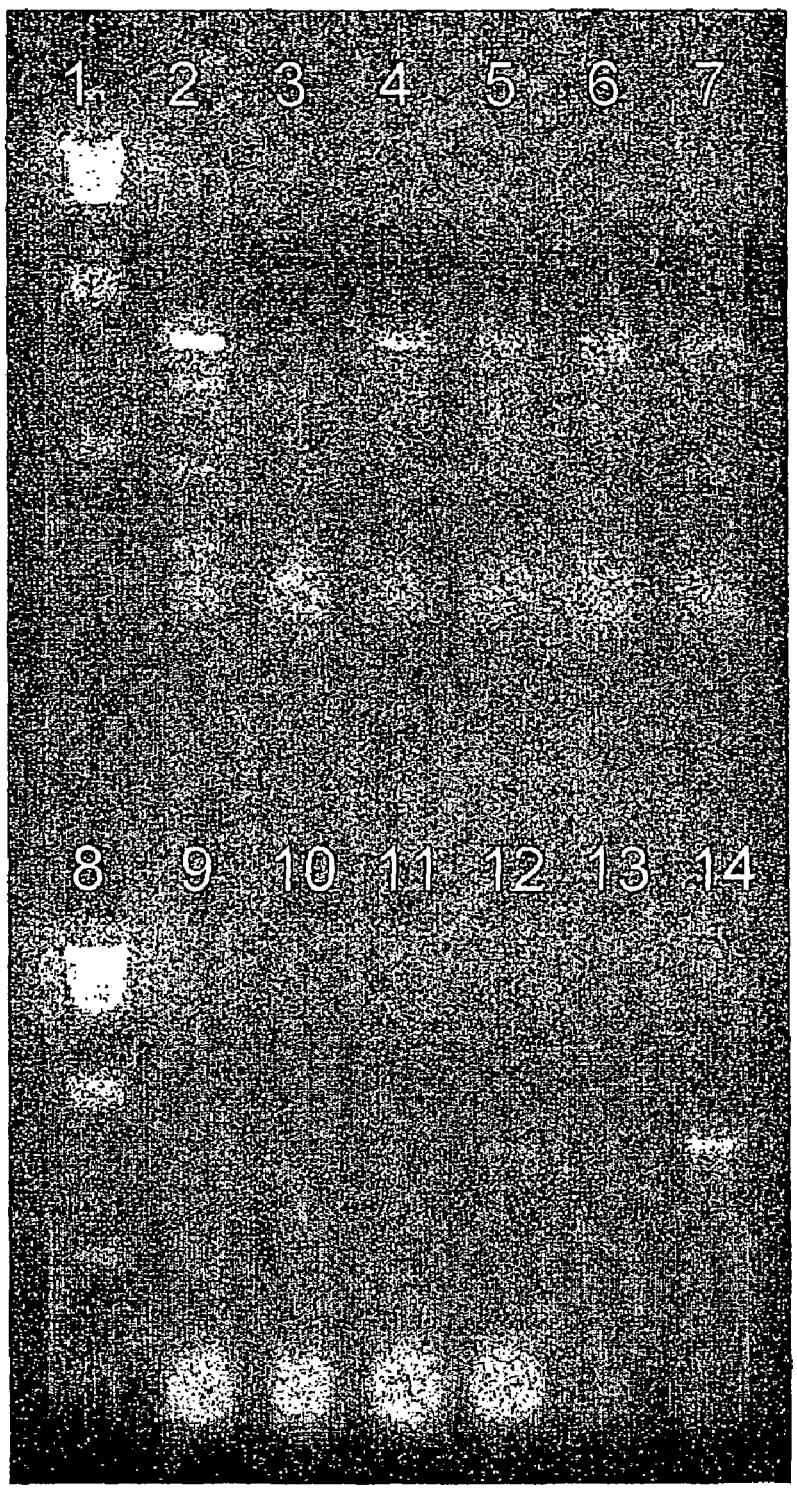
FIG. 9 shows an ethidium bromide-stained agarose gel in which bands were obtained after RT-PCR analysis of AtH1-transformants using total RNA extracted from leaves. On the left-hand side of each panel (i.e., lanes 1 and 8), a molecular size marker (lambda DNA digested with HindIII) is shown. Remaining lanes (lanes 2-7 and 9-14) contain the RT-PCR product obtained from independent transformants. The presence of a 1463 bp DNA fragment indicates the presence of a full-length AtH1 transcript in the transformant.

The PCR positive transformants identified above were further analysed for the presence of full-length AtH1 mRNA in an RT-PCR reaction using total leaf RNA as a template and 5'-GCG TCG ACC CM TGG ACA ACA ACA ACA ACA AC-3' (SEQ ID NO:3) as forward primer and 5'-GCG GAT CCG AGT AGC MT TGC CTA ATT ATC AC-3' (SEQ ID NO:4) as reverse primer. A positive signal was obtained for more than about 70% of the transformants indicating that these transformants accumulate full-length AtH1 mRNA (FIG. 9).

Example 4

Phenotypic Analysis of Grass Transformants Expressing the AtH1 Gene Derived from *Arabidopsis thaliana*

Figure 10:
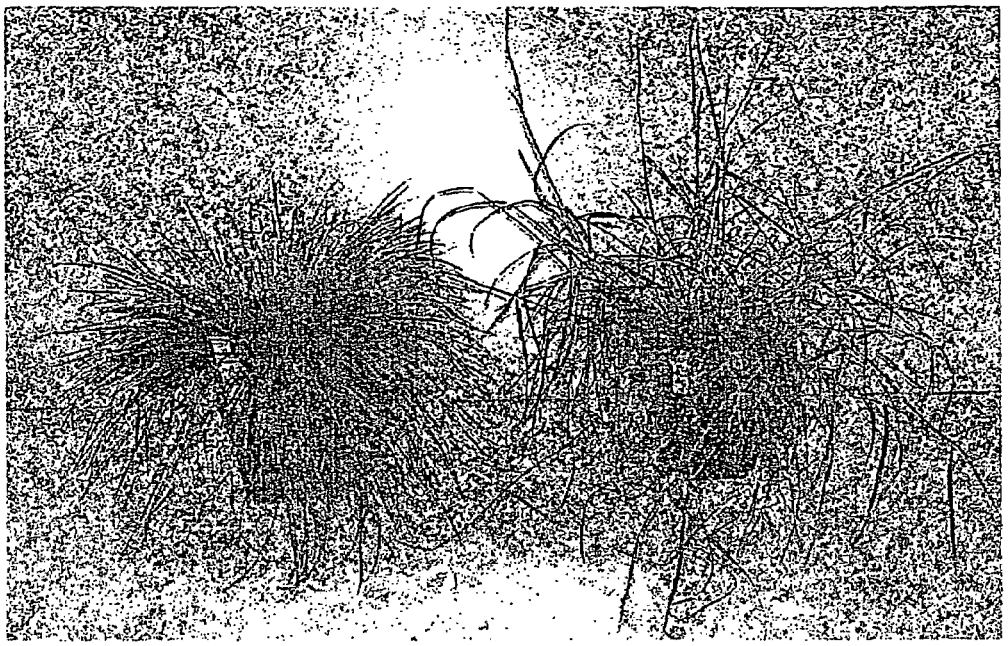
FIG. 10 shows the phenotype of *Lolium perenne* transformants expressing AtH1. The upper panel shows the phenotype of an non-transformed plant (right) and an AtH1-transformant (left) three months after flowering induction. The negative control plant shows an abundant number of inflorescences whereas the AtH1 plant remains completely vegetative. The lower panel shows the phenotype of the AtH1 transformant characterised by a normal habitus and continued vegetative growth.
Figure 10:
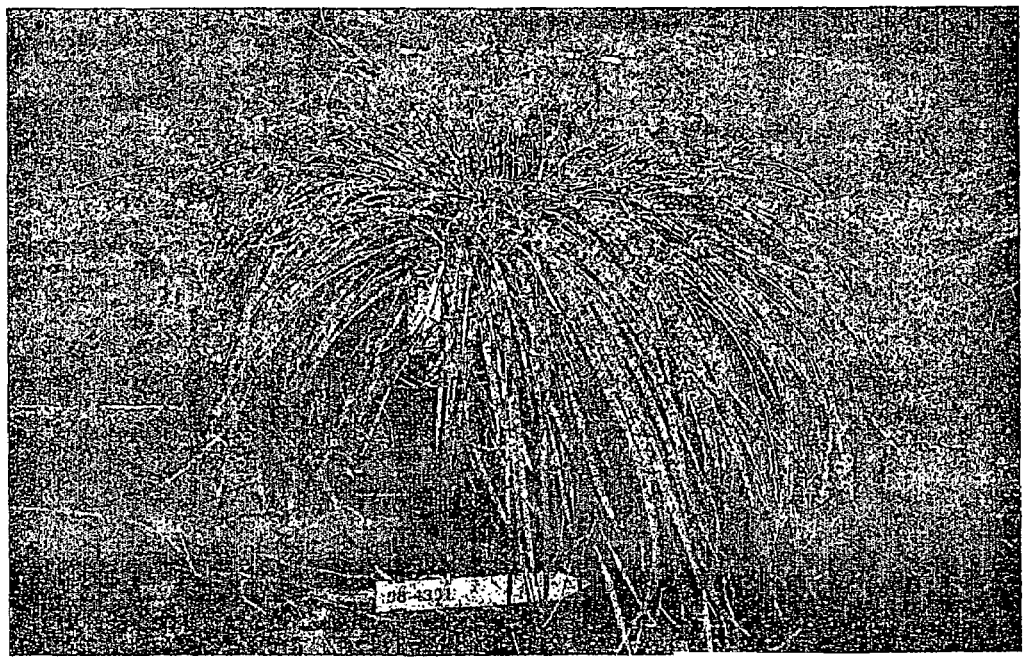

RT-PCR positive plants were vernalised (70 days at 4° C.), together with control plants (RT-PCR negative plants, PCR negative plants, and non-transformed plants). While control plants formed large numbers of inflorescences under Long Day (LD) conditions in the greenhouse (3-6 weeks after transfer from vernalisation to LD conditions), several RT-PCR positive plants continued to form leaves, became very leafy, and had not formed inflorescences 4 months after transfer to LD conditions (FIG. 10). Some RT-PCR positive plants formed only one or two inflorescences about four months after transfer to LD conditions. The overall result is given in Table 4.

TABLE 4

Summary of flowering experiment using AtH1 expressers of *Lolium*

|  | RT-PCR positive plants | Non-transformed control plants |
|---|---|---|
| Total # of plants | 185 | 101 |
| # of non-flowering plants | 34 | 1 |

Example 5

Transformation of *Poa pratensis* L.

Embryogenic suspension cultures of *Poa pratensis* L. (Kentucky bluegrass) (cv. Geronimo) are established according to Nielsen and Knudsen (1998). Genetic transformation for suspension cultures are carried out as described by Spangenberg et al. (1995b) and transformation is with pVDH636, using the particle inflow gun (PIG). The tissue which is transformed is selected, using hygromycin B, according to Spangenberg et al. (1995b).

Example 6

Transformation of *Festuca arundinacea* and *Festuca rubra*

Embryogenic suspension cultures of tall fescue (*Festuca arundinacea* Schreb.) or red fescue (*Festuca rubra* L.) are established, and are then subjected to genetic transformation with pVDH636 according to Spangenberg et al. (1995b). Filters with an embryogenic suspension culture are subjected to bombardment with gold particles coated with the transformation vectors. Transformed tissues can be selected using hygromycin B in accordance with Spangenberg et al. (1995b).

Example 7

Herbicide Resistance as a Trait Linked to a Gene Inhibiting Induction of Flowering in Grasses Transformants exhibiting a clear non-flowering phenotype (i.e., substantial inhibition of flowering under vernalising conditions) were used to demonstrate the functionality in vivo of a transgenic trait increasing chemical resistance of a grass when this trait is genetically linked to the genetic modification. A control group of non-transformed *Lolium* plants as well as a group of clonally propagated transgenic *Lolium* plants transformed with pVDH636 and inhibited in flowering were exposed to a phytotoxic compound through foliar application solution of hygromycin B. The control plants showed severe damage as a consequence of the treatment with hygromycin B. However, the non-flowering transformants are able to survive this treatment as a consequence of the presence of a genetically linked functional hygromycin resistance gene.

Example 8

Genetic Transformation of Grass for Both Inhibition of Generative Propagation and Herbicide Resistance Embryogenic suspension cultures of perennial ryegrass, tall fescue, and red fescue are established as described above, and are genetically transformed, using mixtures of plasmid pVDH636 and pUBA (Toki et al., 1992). Selection of transformed tissues is carried out using hygromycin as described. Non-flowering plants are sprayed with a 1% (v/v) Basta (glufosinate) solution containing 0.1% (v/v) Tween 20 (Toki et al., 1992), in order to detect plants that are both non-flowering and herbicide-resistant.

The usefulness of a non-flowering herbicide-resistant grass is self evident. It avoids the issues of the herbicide resistant being spread to other species of grass or to weeds. The invention can be made with a glufosinate-resistant gene such as Pat or Bar (see EP 0257542 and EP 0275957), a glyphosate gene such as the monocot gene (see U.S. Pat. No. 5,554,798), or a gene of the EPSP class (see U.S. Pat. No. 4,940,835). Additionally, resistance to herbicides containing imidazolinones (e.g., Pursuit), can be introduced with the gene encoding a mutant AHAS enzyme (see U.S. Pat. No. 5,731,180). Furthermore, the combination of (1) a known gene that confers herbicide or pest resistance and (2) a genetic modification which inhibits generative propagation is also envisioned.

Example 9

Reversing Non-Flowering in Grass with Gibberellin

All independent transformed plants, expressing the ATH1-gene, were cloned to form two sets of plants. All plants were vernalized (16 hr dark/8 hr light at 4° C. for 70 days). After the vernalization period the plants were subjected to Long Day conditions (16 hr light/8 hr dark at 18° C.). One set of all transgenics was treated with gibberellic acid (GA3) ($3 \times 10^{-5}$ M GA3 in 5% ethanol by spraying) weekly for four weeks, starting at the start of the LD-period. The other set of plants was sprayed with 5% ethanol. At least some GA3-treated plants are expected to form inflorescences, while the untreated counterparts of the same event will not form inflorescences. This result will show that GA3 can switch the ATH1-induced inhibition of flowering in *L. perenne* to the normal flowering mode. This reversal of phenotype may be enhanced by chemical penetration agents (e.g., DSMO, ethanol, surfactants) or by exposing the meristem to gibberellin by trimming away tillers and other vegetative growth.

Example 10

Relieving Delayed Heading in Grass with Gibberellin

Primary transformants derived from *Lolium perenne* L. (perennial ryegrass) using pVDH636 were vernalized and then subjected to Long Day (LD) conditions in the greenhouse (17 hr light/7 hr dark). Many AtH1-expressing transformants (i.e., RT-PCR positive) showed delayed heading, an important plant characteristic of grass, as compared to non-expressing transformant or non-transformant controls. Several plants failed to flower three months after transfer to LD conditions. AtH1-expressing plants are generally very leafy (FIG. 10).

Several AtH1-expressing transformants (15-20 clones per transformant, three replications), which showed the delayed heading phenotype conferred by the AtH1 transgene, were clonally propagated, vernalised in the winter, and then subjected to a second round of LD conditions the following spring.

Four different gibberellin compounds, which differ in their florigenicity (Evans et al., 1990 were used to treat 3-4 clones per compound and their effect on heading time of transformants and controls was observed. Gibberellin was applied in solvent (5% ethanol supplemented with 0.01% Tween-20 surfactant) at 30 mg/L. It was applied by spraying six times with about 2-3 ml per plant over two weeks, started one week after the beginning of LD conditions. Mean heading time is shown in days after the first spraying. Non-transformant controls were treated with the solvent only.

Transformant (T) and non-transformant (NT) control plants (Table 5) were treated with the indicated gibberellin. GA5 significantly stimulated heading, and GA20 somewhat delayed heading, as compared to non-treated controls. Variation between transformants for their sensitivity to gibberellins could be great.

TABLE 5

Relief of Delayed Heading by Gibberellins (GA)

| Treatment | Mean Heading Time |
|---|---|
| T-GA5 | 33.5[a] |
| T-GA3 | 34.1[ab] |
| T-diHGA5 | 34.2[ab] |
| T-GA20 | 37.8[b] |
| T-no GA | 37.7[b] |
| NT-no GA | 29.9[a] |

Different superscripted letters indicate statistically significant differences in mean heading time (= 0.05 ANOVA).

Transformant (T) plants were grouped into PCR positive (+) or PCR negative (−) for all gibberellin treatments and compared to non-transformant (NT) control plants (Table 6). Only transformants harbouring the AtH1 transgene on average head later than those lacking the gene. Differences between transformants were great. Mean heading times ranged from about 27 days to about 59 days after the first spraying.

TABLE 6

Relief Requires the Presence of the AtH1 Transgene

| Treatment | Mean Heading Time |
|---|---|
| T-PCR(+) | 37.3[b] |
| T-PCR(−) | 33.6[a] |
| NT-no GA | 29.9[a] |

Different superscripted letters indicate statistically significant differences in mean heading time (= 0.05 ANOVA).

Transformant plants were grouped into Taqman assay positive or PCR (+) or Taqman assay negative or PCR (−), and compared to non-transformant control plants (Table 7). This allows differences to be seen between transformants that transcribe or do not transcribe the AtH1 transgene. AtH1-expressing transformants on average head later than those not expressing the transgene. Tissue culture and particle bombardment can also cause delayed heading in *Lolium perenne* (Stadelmann et al., 1998).

TABLE 7

Relief Requires Expression of the AtH1 Transgene

| Treatment | Mean Heading Time |
|---|---|
| PCR (+) expressing | 48.7[c] |
| PCR (−) | 42.6[b] |
| NT | 32.4[a] |

Different superscripted letters indicate statistically significant differences in mean heading time (= 0.05 ANOVA).

REFERENCES

Christensen et al. (1992) Plant Mol. Biol. 18, 675-689
Evans et al. (1990) Planta 182, 97-106
Finer et al. (1992) Plant Cell Reports 11, 323-328
McElroy et al. (1991) Mol. Gen. Genetics 231, 150-160
Nielsen and Knudsen (1998) J. Plant Physiol. 141, 589-595
Quaedviieg et al. (1995) Plant Cell 7, 117-129
Spangenberg et al. (1995a) Plant Science 108, 209-217
Spangenberg et al. (1995b) J. Plant Physiol. 145, 693-701
Stadelmann et al. (1998) Theor. Appl. Genet. 96, 634-639
Toki et al. (1992) Plant Physiol. 100, 1503-1507

All publications cited herein are incorporated by reference and indicate the level of skill in the art.

While the invention has been described in connection with what is presently considered to be practical and preferred embodiments, it should be understood that it is not to be limited or restricted to the disclosed embodiments but, on the contrary, is intended to cover various modifications, substitutions, and combinations within the scope of the appended claims. In this respect, it should be noted that the protection conferred by the claims is determined after their issuance in view of later technical developments and would extend to all legal equivalents.

Therefore, it is to be understood that variations in the invention that are not described herein will be obvious to a person skilled in the art and could be practiced without departing from the invention's novel and non-obvious elements with the proviso that the prior art is excluded.

We claim:

1. A grass which has been genetically modified by introducing a nucleic acid molecule encoding the homeobox transcription factor AtH1 operably linked to a constitutive promoter, wherein said modified grass shows an inhibition of flowering as compared with a grass that has not been genetically modified.

2. The grass according to claim 1, wherein said genetic modification improves at least digestibility or nutritional value or both of the grass with respect to a non-genetically modified plant of the same species.

3. The grass according to claim 1, wherein said genetic modification results in a change in one or more plant characteristics selected from the group consisting of absence of inflorescences, increase in production of tillers, and delay in heading, as compared with a non-genetically modified plant of the same species.

4. The grass according to claim 1, wherein said genetic modification results in an increase in vegetative growth relative to non-genetically modified grass.

5. The grass according to claim 1, wherein the genetic modification lowers the endogenous concentration of gibberellic acid as compared with a non-genetically modified plant of the same species.

6. The grass according to claim 1 which is an amenity-type grass.

7. The grass according to claim 1 which is a forage-type grass.

8. The grass according to claim 7 wherein said grass is a plant species selected from the group consisting of *Dactylis glomerata* L., *Festuca arundinacca* schreb., *Festuca pratensis* huds., *Lolium perenne* L., Loluim multiflorum lam., *Phleum pratense* L., *Agrostis tenuis* sibth., *Festuca rubra* L., *Festuca ovina* ssp. Duriuscula (L.) koch, *Poa pratensis* L., *Poa trivialis* L., *Medicago sativa* L., *Trifolium pratense* L., *Trifolium repens* L., *Agrostis* L. Bermuda, *Agrostis tenais*, and *Agrostis stolonifera*.

9. The progeny of the grass according to claim 1, wherein the progeny stably inherited the genetic modification that substantially inhibited generative propagation.

10. A plant part of the grass according to claim 1, wherein the plant part stably inherited the genetic modification that substantially inhibited generative propagation.

11. The plant part according to claim 9 wherein said plant part is a seed.

12. A method of making the grass according to claim 1 comprising transforming a grass with a nucleic acid molecule that encodes the homeobox transcription factor AtH1 operably linked to a constitutive promoter.

13. A method of using the grass according to claim 1 comprising at least growth or propagation or both of the grass.

14. The method according to claim 13, wherein the grass is used to play at least one sport selected from the group consisting of baseball, cricket, football, golf, rugby, soccer, and tennis.

15. The method according to claim 13, wherein the grass is used at least in a portion of an athletic field, lawn, or park.

16. The method according to claim 13, wherein the grass is fed to an animal selected from the group consisting of a cow, a goat, a horse, and a sheep.

17. The method according to claim 13, wherein the grass is used as animal feedstuff.

\* \* \* \* \*

UNITED STATES PATENT AND TRADEMARK OFFICE
CERTIFICATE OF CORRECTION

PATENT NO. : 7,297,846 B2  
APPLICATION NO. : 10/344975  
DATED : November 20, 2007  
INVENTOR(S) : P. Van Der Valk et al.

It is certified that error appears in the above-identified patent and that said Letters Patent is hereby corrected as shown below:

| COLUMN | LINE | ERROR |
|---|---|---|
| (56) Pg. 1, col. 1 | Refs. Cited (Foreign docs, Item 1) | Delete as duplicative |
| (56) Pg. 1, col. 2 | Refs. Cited (Other Refs., Item 1) | Delete as duplicative |
| (56) Pg. 1, col. 2 | Refs. Cited (Other Refs., Item 2) | "Quaidvilieg" should read --Quaedvlieg-- |
| (56) Pg. 1, col. 2 | Refs. Cited (Other Refs., Item 4) | "World Wide Web." should read --www.-- |
| (56) Pg. 1, col. 2 | Refs. Cited (Other Refs., Item 9) | "81277-1289," should read --8:1277-1289,-- |
| 2 | 12 | "Arabidopis" should read --Arabidopsis-- |
| 2 | 55 | "*saliva*" should read --*sativa*-- |
| 3 | 1 | ""ectoptic" should read --"ectopic-- |
| 4 | 15 | "an non-transformed" should read --a non-transformed-- |
| 5 | 26 | "ahtletic" should read --athletic-- |
| 5 | 39 | "bowling green mown" should read --bowling greens mown-- |

UNITED STATES PATENT AND TRADEMARK OFFICE
CERTIFICATE OF CORRECTION

PATENT NO. : 7,297,846 B2
APPLICATION NO. : 10/344975
DATED : November 20, 2007
INVENTOR(S) : P. Van Der Valk et al.

It is certified that error appears in the above-identified patent and that said Letters Patent is hereby corrected as shown below:

| COLUMN | LINE | ERROR |
|---|---|---|
| 5 | 56 | "enhance its useful" should read --enhance its usefulness-- |
| 5 | 58 | "the Invention" should read --the invention-- |
| 6 | 20 | "fecsue" should read --fescue-- |
| 6 | 28 | "surface, (a uniform sward)" should read --surface (a uniform sward),-- |
| 6 | 38 | after "pollination" delete "," |
| 7 | 30 | "acid:" should read --acid.-- |
| 7 | 62 | "a usefully" should read --a useful-- |
| 7 | 63 | "monocots" should read --monocot-- |
| 7 | 64 | "a inexpensive" should read --an inexpensive-- |
| 7 | 67 | "However, upon expression in of the" should read --Upon expression,-- |
| 8 | 7-8 | "species including Grass" should read --species, including grass,-- |
| 9 | 31-32 | "biomass is containing" should read --biomass contains-- |
| 10 | 15 | "Bg/II" should read --*Bgl*II-- |
| 10 | 17 | "AtHI" should read --AtHl-- |
| 10 | 23 | "CM" should read --CAA-- |

UNITED STATES PATENT AND TRADEMARK OFFICE
CERTIFICATE OF CORRECTION

PATENT NO. : 7,297,846 B2
APPLICATION NO. : 10/344975
DATED : November 20, 2007
INVENTOR(S) : P. Van Der Valk et al.

It is certified that error appears in the above-identified patent and that said Letters Patent is hereby corrected as shown below:

| COLUMN | LINE | ERROR |
|---|---|---|
| 10 | 25 | "MT" should read --AAT-- |
| 10 | 27 | "Sa/I" should read --*Sal*I-- |
| 10 | 28 | "Sa/I" should read --*Sal*I-- |
| 10 | 30 | "Sa/I" should read --*Sal*I-- [both instances] |
| 10 | 32 | "AtHI" should read --AtHl-- |
| 10 | 34 | "locate at" should read --located at-- |
| 10 | 39 | "AtHI" should read --AtHl-- |
| 10 | 41 | "AtHI" should read --AtHl-- |
| 11 | 65 | "CM" should read --CAA-- |
| 11 | 67 | "MT" should read --AAT-- |
| 12 | 2 | "AtH" should read --AtHl-- |
| 12 | 16 | "CM" should read --CAA-- |
| 12 | 18 | "MT" should read --AAT-- |
| 14 | 22 | "DSMO" should read --DMSO-- |
| 16 | 21 | "Quaedviieg" should read --Quaedvlieg-- |

UNITED STATES PATENT AND TRADEMARK OFFICE
CERTIFICATE OF CORRECTION

PATENT NO. : 7,297,846 B2
APPLICATION NO. : 10/344975
DATED : November 20, 2007
INVENTOR(S) : P. Van Der Valk et al.

It is certified that error appears in the above-identified patent and that said Letters Patent is hereby corrected as shown below:

| COLUMN | LINE | ERROR |
|---|---|---|
| 29 (Claim 8, | 3 line 3) | "*L.*," should read --*L.*,-- |
| 29 (Claim 8, | 3 line 3) | "arundinacca" should read --arundinacea-- |
| 29 (Claim 8, | 4 line 4) | "Lolium multiflorum" should read --*Lolium multiflorum*-- |
| 29 (Claim 8, | 8 line 8) | "*tenais*," should read --*tenuis*,-- |
| 29 (Claim 11, | 16 line 1) | "claim 9" should read --claim 10-- |

Signed and Sealed this

Sixth Day of May, 2008

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 9359
<212> TYPE: DNA
<213> ORGANISM: Artificial Sequence
<220> FEATURE:
<223> OTHER INFORMATION: Vector pVDH636 nucleotide sequence
<220> FEATURE:
<221> NAME/KEY: gene
<222> LOCATION: (839)..(1699)
<223> OTHER INFORMATION: Beta-lactamase gene (AmpR)
<220> FEATURE:
<221> NAME/KEY: gene
<222> LOCATION: (8085)..(9119)
<223> OTHER INFORMATION: Hygromycin resistance gene from Escherichia
      coli
<220> FEATURE:
<221> NAME/KEY: polyA_signal
<222> LOCATION: (9120)..(9359)
<223> OTHER INFORMATION: PolyA signal from 35S gene from Cauliflower
      mosaic virus
```

```
<220> FEATURE:
<221> NAME/KEY: promoter
<222> LOCATION: (2941)..(4920)
<223> OTHER INFORMATION: Ubi-promoter from maize
<220> FEATURE:
<221> NAME/KEY: gene
<222> LOCATION: (4921)..(6400)
<223> OTHER INFORMATION: AtH1 gene from Arabidopsis thaliana
<220> FEATURE:
<221> NAME/KEY: polyA_signal
<222> LOCATION: (6401)..(6672)
<223> OTHER INFORMATION: Poly-A signal from the nopaline synthetase gene
      from Agrobacterium tumefaciens
<220> FEATURE:
<221> NAME/KEY: misc_feature
<222> LOCATION: (7434)..(8084)
<223> OTHER INFORMATION: First exon-intron combination from Ubi-maize

<400> SEQUENCE: 1
aattcgggcc caattcgccc tatagtgagt cgtattacaa ttcactggcc gtcgttttac      60
aacgtcgtga ctgggaaaac cctggcgtta cccaacttaa tcgccttgca gcacatcccc     120
cttttcgcca gctggcgtaat agcgaagagg cccgcaccga tcgcccttcc caacagttgc    180
gcagcctgaa tggcgaatgg acgcgccctg tagcggcgca ttaagcgcgg cgggtgtggt     240
ggttacgcgc agcgtgaccg ctacacttgc cagcgcccta gcgcccgctc ctttcgcttt     300
cttcccttcc tttctcgcca cgttcgccgg ctttccccgt caagctctaa atcgggggct    360
ccctttaggg ttccgatttta gtgctttacg gcacctcgac cccaaaaaac ttgattaggg    420
tgatggttca cgtagtgggc catcgccctg atagacggtt tttcgccctt tgacgttgga    480
gtccacgttc tttaatagtg gactcttgtt ccaaactgga caacactca accctatctc     540 ggtctattct tttgatttat aagggatttt gccgatttcg gcctattggt taaaaaatga    600
gctgatttaa caaaaattta acgcgaattt taacaaaata ttaacgctta caattcctg    660 atgcggtatt ttctccttac gcatctgtgc ggtatttcac accgcatcag gtggcacttt     720
tcggggaaat gtgcgcggaa cccctatttg tttattttc taaatacatt caaatatgta    780
tccgctcatg agacaataac cctgataaat gcttcaataa tattgaaaaa ggaagagtat    840
gagtattcaa catttccgtg tcgcccttat ccctttttt gcggcatttt gccttcctgt     900
ttttgctcac ccagaaacgc tggtgaaagt aaaagatgct gaagatcagt tgggtgcacg    960
agtgggttac atcgaactgg atctcaacag cggtaagatc cttgagagtt ttcgccccga   1020
agaacgtttt ccaatgatga gcacttttaa agttctgcta tgtggcgcgg tattatcccg    1080
tattgacgcc gggcaagagc aactcggtcg ccgcatacac tattctcaga atgacttggt    1140
tgagtactca ccagtcacag aaaagcatct tacggatggc atgacagtaa gagaattatg    1200
cagtgctgcc ataaccatga gtgataacac tgcggccaac ttacttctga caacgatcgg    1260
aggaccgaag gagctaaccg cttttttgca acatggggg atcatgtaa ctcgccttga    1320 tcgttgggaa ccggagctga atgaagccat accaaacgac gagcgtgaca ccacgatgcc    1380
tgtagcaatg gcaacaacgt tgcgcaaact attaactggc gaactactta ctctagcttc    1440
ccggcaacaa ttaatagact ggatggaggc ggataaagtt gcaggaccac ttctgcgctc    1500
ggcccttccg gctggctggt ttattgctga taaatctgga gccggtgagc gtgggtctcg    1560
cggtatcatt gcagcactgg ggccagatgg taagccctcc cgtatcgtag ttatctacac    1620
gacggggagt caggcaacta tggatgaacg aaatagacag atcgctgaga taggtgcctc    1680
actgattaag cattggtaac tgtcagacca agtttactca tatatacttt agattgattt    1740
aaaacttcat ttttaattta aaaggatcta ggtgaagatc cttttttgata atctcatgac    1800
```

-continued

```
caaaatccct taacgtgagt tttcgttcca ctgagcgtca gaccccgtag aaaagatcaa   1860
aggatcttct tgagatcctt tttttctgcg cgtaatctgc tgcttgcaaa caaaaaaacc   1920
accgctacca gcggtggttt gtttgccgga tcaagagcta ccaactcttt ttccgaaggt   1980
aactggcttc agcagagcgc agataccaaa tactgttctt ctagtgtagc cgtagttagg   2040
ccaccacttc aagaactctg tagcaccgcc tacatacctc gctctgctaa tcctgttacc   2100
agtggctgct gccagtggcg ataagtcgtg tcttaccggg ttggactcaa gacgatagtt   2160
accggataag cgcagcggt cgggctgaac ggggggttcg tgcacacagc ccagcttgga   2220
gcgaacgacc tacaccgaac tgagatacct acagcgtgag ctatgagaaa gcgccacgct   2280
tcccgaaggg agaaaggcgg acaggtatcc ggtaagcggc agggtcggaa caggagagcg   2340
cacgagggag cttccagggg gaaacgcctg gtatctttat agtcctgtcg ggtttcgcca   2400
cctctgactt gagcgtcgat ttttgtgatg ctcgtcaggg gggcggagcc tatggaaaaa   2460
cgccagcaac gcggccttttt tacggttcct ggccttttgc tggccttttg ctcacatgtt   2520
ctttcctgcg ttatccctg attctgtgga taaccgtatt accgcctttg agtgagctga   2580
taccgctcgc cgcagccgaa cgaccgagcg cagcgagtca gtgagcgagg aagcggaaga   2640
gcgcccaata cgcaaaccgc ctctccccgc gcgttggccg attcattaat gcagctggca   2700
cgacaggttt cccgactgga aagcgggcag tgagcgcaac gcaattaatg tgagttagct   2760
cactcattag gcaccccagg ctttacactt tatgcttccg gctcgtatgt tgtgtggaat   2820
tgtgagcgga taacaatttc acacaggaaa cagctatgac catgattacg ccaagctatt   2880
taggtgacac tatagaatac tcaagctatg catccaacgc gttgggagct ctcccatatg   2940
gtcgacctgc aggcggccgc ctagagataa tgagcattgc atgtctaagt tataaaaaat   3000
taccacatat ttttttttgtc acacttgttt gaagtgcagt ttatctatct ttatacatat   3060
atttaaactt tactctacga ataatataat ctatagtact acaataatat cagtgtttta   3120
gagaatcata taaatgaaca gttagacatg gtctaaagga caattgagta ttttgacaac   3180
aggactctac agttttatct ttttagtgtg catgtgttct ccttttttttt tgcaaatagc   3240 ttcacctata taatacttca tccattttat tagtacatcc atttagggtt tagggttaat   3300
ggtttttata gactaatttt tttagtacat ctattttatt ctattttagc ctctaaatta   3360
agaaaactaa aactctatttt tagttttttt atttaataat ttagatataa aatagaataa   3420
aataaagtga ctaaaaatta aacaaatacc ctttaagaaa ttaaaaaaac taaggaaaca   3480
tttttcttgt ttcgagtaga taatgccagc ctgttaaacg ccgtcgacga gtctaacgga   3540
caccaaccag cgaaccagca gcgtcgcgtc gggccaagcg aagcagacgg cacggcatct   3600
ctgtcgctgc ctctggaccc ctctcgagag ttccgctcca ccgttggact tgctccgctg   3660
tcggcatcca gaaattgcgt ggcggagcgg cagacgtgag ccggcacggc aggcggcctc   3720
ctcctcctct cacggcaccg gcagctacgg gggattcctt tcccaccgct ccttcgcttt   3780
cccttcctcg cccgccgtaa taaatagaca ccccctccac accctctttc cccaacctcg   3840
tgttgttcgg agcgcacaca cacacaacca gatctccccc aaatccaccc gtcggcacct   3900
ccgcttcaag gtacgccgct cgtcctcccc cccccccct ctctaccttc tctagatcgg   3960
cgttccggtc catggttagg gcccggtagt tctacttctg ttcatgtttg tgttagatcc   4020
gtgtttgtgt tagatccgtg ctgctagcgt tcgtacacgg atgcgacctg tacgtcagac   4080
acgttctgat tgctaacttg ccagtgtttc tctttgggga atcctgggat ggctctagcc   4140
```

```
gttccgcaga cgggatcgat ttcatgattt tttttgtttc gttgcatagg gtttggtttg   4200
cccttttcct ttatttcaat atatgccgtg cacttgtttg tcgggtcatc ttttcatgct   4260 ttttttttgtc ttggttgtga tgatgtggtc tggttgggcg gtcgttctag atcggagtag   4320
aattctgttt caaactacct ggtggattta ttaattttgg atctgtatgt gtgtgccata   4380
catattcata gttacgaatt gaagatgatg gatggaaata tcgatctagg ataggtatac   4440
atgttgatgc gggttttact gatgcatata cagagatgct ttttgttcgc ttggttgtga   4500
tgatgtggtg tggttgggcg gtcgttcatt cgttctagat cggagtagaa tactgtttca   4560
aactacctgg tgtatttatt aattttggaa ctgtatgtgt gtgtcataca tcttcatagt   4620
tacgagttta agatggatgg aaatatcgat ctaggatagg tatacatgtt gatgtgggtt   4680
ttactgatgc atatacatga tggcatatgc agcatctatt catatgctct aaccttgagt   4740
acctatctat tataataaac aagtatgttt tataattatt ttgatcttga tatacttgga   4800
tgatggcata tgcagcagct atatgtggat tttttagcc ctgccttcat acgctattta   4860
tttgcttggt actgtttctt ttgtcgatgc tcaccctgtt gtttggtgtt acttctgcag   4920
gtcgacccaa tggacaacaa caacaacaac aacactttta gttctctgga taatgtcatg   4980
actaaccaaa atcctcttct catggatttt ataccttcaa gagaagattc aacttcattc   5040
tcaacaatgc ttccatggaa taccatcaga tcagatcctc tacaaatggg tggctttgat   5100
attttcaatt ctatgctgac taacaaatac ttatcatctt ctccacggtc tatcgatgtt   5160
caagataacc gcaatgttga gttcatggct cctcctcctc atcctcctcc acttcatcct   5220
ttggatcatt taagacacta tgatgattcc tcaaacaaca tgtggggttt tgaagcaaat   5280
agtgagtttc aggcattttc aggtgtagtt ggtccaagtg aaccaatgat gtctacattc   5340
ggtgaagaag atttcccgtt tctaatttcg aataaaagaa acaatgagct ttcattgagt   5400
cttgcatcag atgtttctga tgaatgctcg gagataagtc tttgtgcagc tacaagatta   5460
gcctcagagc aagcttcttg cagcagcaaa gacatttcta ataacgttgt tactcaaggt   5520
ttctctcaac ttatatttgg ctcaaaatac cttcactctg ttcaagaaat actatctcat   5580
ttcgccgcat actcgctcga ttattcatct cgaggaaccg agtcaggagc tgctagttca   5640
gcctttactt cacgttttga aatataact gagtttcttg atggtgattc taataactcg   5700
gaggcgggtt tcggatctac atttcaaagg agagcattag aagcaaagaa acccatctc   5760 ttggatcttc ttcaaatggt ggatgatcga tatagtcatt gcgtagatga gattcatacg   5820
gttatatcag cgttccatgc tgcaaccgag ttagatccac agttacacac ccggtttgcc   5880
ctccaaaccg tttccttctt atacaagaac ctgagagaga gaatctgcaa gaagataatc   5940
tctatgggat ctgtattgga gagagcaaa gacaagactc aagaaacctc tatgttccac   6000
cagcattgcc ttcttcagca gctgaaacga aagaaccatc agatttggag acctcaacga   6060
ggtttgcctg agaaatctgt ttcggttcta cggaattgga tgttccaaaa cttccttcac   6120
ccttacccga aagattcgga gaaacatctt ctagctatac gaagtggctt gacaagaagt   6180
caggtatcaa actggtttat aaatgcgcgg gttaggctat ggaagccgat gatagaagag   6240
atgtatgcgg aaatgaacaa gaggaagctc aataacagtc acattcaacc caacggacca   6300
actcttcgaa tgccaaaatc tgttatgatg agccaagcaa tgcataaata agacaacaat   6360
tgtgtttacc aactttgtga taattaggca attgctactc ggatccccga tcgttcaaac   6420
atttggcaat aaagtttctt aagattgaat cctgttgccg tcttgcgat gattatcata   6480 taatttctgt tgaattacgt taagcatgta ataattaaca tgtaatgcat gacgttattt   6540
```

```
atgagatggg ttttatgat tagagtcccg caattataca tttaatacgc gatagaaaac    6600
aaaatatagc gcgcaaacta ggataaatta tcgcgcgcgg tgtcatctat gttactagat    6660
cgatcgggaa ttgcggccgc actagcatac tcgaggtcat tcatatgctt gagaagagag    6720
tcgggatagt ccaaaataaa acaaaggtaa gattacctgg tcaaaagtga aacatcagt     6780
taaaaggtgg tataaagtaa aatatcggta ataaaaggtg gcccaaagtg aaatttactc    6840
ttttctacta ttataaaaat tgaggatgtt tttgtcggta ctttgatacg tcattttga     6900
tgaattggtt tttaagttta ttcgcttttg gaaatgcata tctgtatttg aatcgggttt    6960
taagttcgtt tgcctttgta aatacagagg gatttgtata agaaatatct ttaaaaaaac    7020
ccatatgcta atttgacata attttttgaga aaaatatata ttcaggcgaa ttctcacaat    7080
gaacaataat aagattaaaa tagctttccc ccgttgcagc gcatgggtat tttttctagt    7140
aaaaataaaa gataaactta gactcaaaac atttacaaaa acaaccccta aagttcctaa    7200
agcccaaagt gctatccacg atccatagca abcccagccc aacccaaccc aacccaaccc    7260
accccagtcc agccaactgg acaatagtct ccabdccccc ccactatcac cgtgagttgt    7320
ccgcacgcac cgcacgtctc gcagccaaaa aaaaaaaaaa gaaagaaaaa aaagaaaaag    7380
aaaaaacagc aggtgggtcc gggtcgtggg ggccggaaac gcgaggagga tcgcgagcca    7440
gcgacgaggc cggccctccc tccgcttcca agaaacgcc ccccatcgcc actatataca    7500
tacccccccc tctcctccca tcccccccaac cctaccacca ccaccaccac cacctccacc    7560
tcctcccccc tcgctgccgg acgacgagct cctccccccct cccctccgc cgccgccgcg    7620
ccggtaacca ccccgcccct ctcctctttc tttctccgtt ttttttttccg tctcggtctc    7680
gatctttggc cttggtagtt tgggtgggcg agaggcggct tcgtgcgcgc ccagatcggt    7740
gcgcgggagg ggcgggatct cgcggctggg gctctcgccg gcgtggatcc ggcccggatc    7800
tcgcggggaa tggggctctc ggatgtagat ctgcgatccg ccgttgttgg gggagatgat    7860
gggggggttta aaatttccgc catgctaaac aagatcagga agagggaaa agggcactat    7920
ggtttatatt tttatatatt tctgctgctt cgtcaggctt agatgtgcta gatctttctt    7980
tcttcttttt gtgggtagaa tttgaatccc tcagcattgt tcatcggtag ttttttcttt    8040
catgatttgt gacaaatgca gcctcgtgcg gagcttttt gtaggtagac cggggggcaa    8100
tgagatatga aaaagcctga actcaccgcg acgtctgtcg agaagtttct gatcgaaaag    8160
ttcgacagcg tctccgacct gatgcagctc tcggagggcg aagaatctcg tgctttcagc    8220
ttcgatgtag agggcgtgg atatgtctgc gggtaaatag tgcgccgatg gtttctacaa    8280
agatcgttat gtttatcggc actttgcatc ggccgcgctc ccgattccgg aagtgcttga    8340
cattggggaa ttcagcgaga gcctgaccta ttgcatctcc cgccgtgcac agggtgtcac    8400
gttgcaagac ctgcctgaaa ccgaactgcc cgctgttctg cagccggtcg cggaggccat    8460
ggatgcgatc gctgcggccg atcttagcca gacgagcggg ttcggcccat tcggaccgca    8520
aggaatcggt caatcacta catggcgtga tttcatatgc gcgattgctg atccccatgt    8580
gtatcactgg caaactgtga tggacgacac cgtcagtgcg tccgtcgcgc aggctctcga    8640
tgagctgatg ctttgggccg aggactgccc cgaagtccgg cacctcgtgc acgcggattt    8700
cggctccaac aattgcctga cggacaatgg ccgcataaca gcggtcattg actggagcga    8760
ggcgatgttc ggggattccc aatacgaggt cgccaacatc ttcttctgga ggccgtggtt    8820
ggcttgtatg gagcagcaga cgcgctactt cgagcggagg catccggagc ttgcaggatc    8880
```

```
gccgcggctc cgggcgtata tgctccgcat tggtcttgac caactctatc agagcttggt    8940
tgacggcaat ttcgatgatg cagcttgggc gcagggtcga tgcgacgcaa tcgtccgatc    9000
cggagccggg actgtcgggc gtacacaaat cgcccgcaga agcgcggccg gccgtctgga    9060
ccgatggctg tgtagaagta ctcgccgata gtggaaaccg acgccccagc actcgtccgg    9120
gatcctctag agtcgacctg caggcatgcc cgctgaaatc accagtctct ctctacaaat    9180
ctatctctct ctataataat gtgtgagtag ttcccagata agggaattag ggttcttata    9240
gggtttcgct catgtgttga gcatataaga aaccttagt atgtatttgt atttgtaaaa     9300
tacttctatc aataaaattt ctaattccta aaaccaaaat ccaggggtac ccgagctcg     9359
```

<210> SEQ ID NO 2
<211> LENGTH: 473
<212> TYPE: PRT
<213> ORGANISM: Arabidopsis Thaliana

<400> SEQUENCE: 2

```
Met Asp Asn Asn Asn Asn Asn Thr Phe Ser Ser Leu Asp Asn Val
1               5                   10                  15

Met Thr Asn Gln Asn Pro Leu Leu Met Asp Phe Ile Pro Ser Arg Glu
            20                  25                  30

Asp Ser Thr Ser Phe Ser Thr Met Leu Pro Trp Asn Thr Ile Arg Ser
        35                  40                  45

Asp Pro Leu Gln Met Gly Gly Phe Asp Ile Phe Asn Ser Met Leu Thr
    50                  55                  60

Asn Lys Tyr Leu Ser Ser Ser Pro Arg Ser Ile Asp Val Gln Asp Asn
65                  70                  75                  80

Arg Asn Val Glu Phe Met Ala Pro Pro His Pro Pro Leu His
                85                  90                  95

Pro Leu Asp His Leu Arg His Tyr Asp Asp Ser Ser Asn Asn Met Trp
            100                 105                 110

Gly Phe Glu Ala Asn Ser Glu Phe Gln Ala Phe Ser Gly Val Val Gly
        115                 120                 125

Pro Ser Glu Pro Met Met Ser Thr Phe Gly Glu Asp Phe Pro Phe
    130                 135                 140

Leu Ile Ser Asn Lys Arg Asn Asn Glu Leu Ser Leu Ser Leu Ala Ser
145                 150                 155                 160

Asp Val Ser Asp Glu Cys Ser Glu Ile Ser Leu Cys Ala Ala Thr Arg
                165                 170                 175

Leu Ala Ser Glu Gln Ala Ser Cys Ser Ser Lys Asp Ile Ser Asn Asn
            180                 185                 190

Val Val Thr Gln Gly Phe Ser Gln Leu Ile Phe Gly Ser Lys Tyr Leu
        195                 200                 205

His Ser Val Gln Glu Ile Leu Ser His Phe Ala Ala Tyr Ser Leu Asp
    210                 215                 220

Tyr Ser Ser Arg Gly Thr Glu Ser Gly Ala Ala Ser Ser Ala Phe Thr
225                 230                 235                 240

Ser Arg Phe Glu Asn Ile Thr Glu Phe Leu Asp Gly Asp Ser Asn Asn
                245                 250                 255

Ser Glu Ala Gly Phe Gly Ser Thr Phe Gln Arg Arg Ala Leu Glu Ala
            260                 265                 270

Lys Lys Thr His Leu Leu Asp Leu Leu Gln Met Val Asp Asp Arg Tyr
        275                 280                 285

Ser His Cys Val Asp Glu Ile His Thr Val Ile Ser Ala Phe His Ala
```

```
                290               295               300
Ala Thr Glu Leu Asp Pro Gln Leu His Thr Arg Phe Ala Leu Gln Thr
305                 310                 315                 320

Val Ser Phe Leu Tyr Lys Asn Leu Arg Glu Arg Ile Cys Lys Lys Ile
                325                 330                 335

Ile Ser Met Gly Ser Val Leu Glu Arg Gly Lys Asp Lys Thr Gln Glu
                340                 345                 350

Thr Ser Met Phe His Gln His Cys Leu Leu Gln Gln Leu Lys Arg Lys
                355                 360                 365

Asn His Gln Ile Trp Arg Pro Gln Arg Gly Leu Pro Glu Lys Ser Val
    370                 375                 380

Ser Val Leu Arg Asn Trp Met Phe Gln Asn Phe Leu His Pro Tyr Pro
385                 390                 395                 400

Lys Asp Ser Glu Lys His Leu Leu Ala Ile Arg Ser Gly Leu Thr Arg
                405                 410                 415

Ser Gln Val Ser Asn Trp Phe Ile Asn Ala Arg Val Arg Leu Trp Lys
                420                 425                 430

Pro Met Ile Glu Glu Met Tyr Ala Glu Met Asn Lys Arg Lys Leu Asn
                435                 440                 445

Asn Ser His Ile Gln Pro Asn Gly Pro Thr Leu Arg Met Pro Lys Ser
    450                 455                 460

Val Met Met Ser Gln Ala Met His Lys
465                 470

<210> SEQ ID NO 3
<211> LENGTH: 30
<212> TYPE: DNA
<213> ORGANISM: Artificial Sequence
<220> FEATURE:
<223> OTHER INFORMATION: AtH1 cDNA Forward Primer

<400> SEQUENCE: 3
gcgtcgaccc aatggacaac aacaacaaca                                      30

<210> SEQ ID NO 4
<211> LENGTH: 32
<212> TYPE: DNA
<213> ORGANISM: Artificial Sequence
<220> FEATURE:
<223> OTHER INFORMATION: AtH1 cDNA Reverse Primer

<400> SEQUENCE: 4
gcggatccga gtagcaattg cctaattatc ac                                   32
```